US007358014B2

(12) United States Patent
Law et al.

(10) Patent No.: US 7,358,014 B2
(45) Date of Patent: Apr. 15, 2008

(54) ELECTROPHOTOGRAPHIC ORGANOPHOTORECEPTORS WITH NOVEL CHARGE TRANSPORT COMPOUNDS

(75) Inventors: Kam W. Law, San Diego, CA (US); Nusrallah Jubran, St. Paul, MN (US); Zbigniew Tokarski, Woodbury, MN (US); Alan R. Katritzky, Gainesville, FL (US); Ritu Jain, Gaineville, FL (US); Rexiat Maimait, Folsom, CA (US)

(73) Assignee: Samsung Electronics Co., Ltd., Kyungki-Do (KR)

( * ) Notice: Subject to any disclaimer, the term of this patent is extended or adjusted under 35 U.S.C. 154(b) by 65 days.

(21) Appl. No.: 10/215,359

(22) Filed: Aug. 9, 2002

(65) Prior Publication Data

US 2003/0113132 A1 Jun. 19, 2003

Related U.S. Application Data

(60) Provisional application No. 60/330,381, filed on Oct. 18, 2001, provisional application No. 60/325,716, filed on Sep. 28, 2001, provisional application No. 60/323,781, filed on Sep. 20, 2001, provisional application No. 60/323,782, filed on Sep. 20, 2001, provisional application No. 60/317,088, filed on Sep. 4, 2001, provisional application No. 60/317,086, filed on Sep. 4, 2001, provisional application No. 60/314,047, filed on Aug. 22, 2001, provisional application No. 60/314,055, filed on Aug. 22, 2001, provisional application No. 60/311,601, filed on Aug. 10, 2001.

(51) Int. Cl.
*G03G 5/047* (2006.01)
(52) U.S. Cl. ............... 430/58.15; 430/58.4; 430/58.45; 430/58.5; 430/58.55; 430/58.6; 430/79; 399/162
(58) Field of Classification Search .................. 430/79, 430/58.15, 58.45, 58.55, 58.6, 58.4, 58.5; 548/251, 257, 364.7, 444, 364.1; 399/162, 399/159
See application file for complete search history.

(56) References Cited

U.S. PATENT DOCUMENTS

| | | | |
|---|---|---|---|
| 4,297,426 A | 10/1981 | Sakai et al. | |
| 4,463,077 A * | 7/1984 | Matsuura et al. | 430/56 |
| 4,476,137 A | 10/1984 | Haviv et al. | 424/272 |
| 4,786,571 A | 11/1988 | Ueda | 430/81 |
| 4,957,838 A | 9/1990 | Aruga et al. | |
| 5,128,227 A | 7/1992 | Monbaliu et al. | 430/59 |
| 5,274,116 A | 12/1993 | Martin et al. | 548/465 |
| 5,422,210 A | 6/1995 | Maruyama et al. | 430/66 |
| 5,618,646 A * | 4/1997 | Nogami et al. | 430/58.5 |
| 5,737,669 A * | 4/1998 | Ring | 399/162 |
| 5,932,384 A | 8/1999 | Mistsumori et al. | 430/83 |
| 6,001,522 A | 12/1999 | Woo et al. | 430/65 |
| 6,020,096 A | 2/2000 | Fuller et al. | 430/58.35 |

(Continued)

FOREIGN PATENT DOCUMENTS

EP 0 707 238 A1 4/1996

(Continued)

OTHER PUBLICATIONS

Japanese Patent Office Machine-Assisted Translation of JP 9-43879 (pub Feb. 14, 1997).*

(Continued)

*Primary Examiner*—Janis L. Dote
(74) *Attorney, Agent, or Firm*—Patterson, Thuente, Skaar & Christensen, P.A.

(57) ABSTRACT

A novel charge transport compound, a novel process using that novel compound and an organophotoreceptor includes:
(a) a novel charge transport compound having the formula

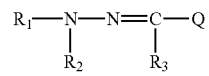

where $R_1$ and $R_2$ are selected so that $R_1$ and $R_2$ form, with the included nitrogen atom, a group selected from the group consisting of heterocyclic rings, aromatic rings, and dinaphthylamine; or $R_1$ comprises an aryl group and $R_2$ comprises a group selected from the group consisting of sulfolanyl, pyrrolyl, pyrazolyl, benzotriazolyl, stilbenyl, tetrazolyl, and group A, wherein group A is represented by the structure

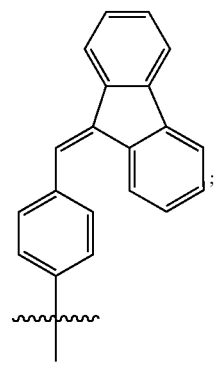

or $R_1$ comprises hydrogen, alkyl group, aryl group and $R_2$ comprises sulfonylphenyl.
$R_3$ is hydrogen, alkyl group, aryl group, a heterocyclic group or a hydrocarbon group; and
Q is a 3-carbazole group;
(b) a charge generating compound; and
(c) an electrically conductive substrate.

36 Claims, No Drawings

U.S. PATENT DOCUMENTS

| | | | |
|---|---|---|---|
| 6,030,734 A | 2/2000 | Mitsumori | 430/58.8 |
| 6,066,426 A | 5/2000 | Mott et al. | 430/58.2 |
| 6,099,996 A | 8/2000 | Yanus et al. | 430/58.8 |
| 6,140,004 A | 10/2000 | Mott et al. | 430/132 |
| 6,214,503 B1 | 4/2001 | Gaidelis et al. | 430/58.45 |
| 6,340,548 B1 | 1/2002 | Jubran et al. | 430/58.45 |
| 6,864,025 B2 * | 3/2005 | Law et al. | 430/58.6 |
| 2003/0113643 A1 * | 6/2003 | Law et al. | 430/58.15 |
| 2003/0113644 A1 * | 6/2003 | Law et al. | 430/58.15 |
| 2003/0207188 A1 * | 11/2003 | Jubran et al. | 430/58.15 |

FOREIGN PATENT DOCUMENTS

| | | | |
|---|---|---|---|
| GB | 1047525 | | 11/1966 |
| GB | 2249789 A | | 5/1992 |
| JP | 64-082045 | | 3/1989 |
| JP | 01-126654 | | 5/1989 |
| JP | 04-246654 | | 9/1992 |
| JP | 9-43879 | * | 2/1997 |
| JP | 10-133399 | | 5/1998 |
| JP | 5-148210 | | 6/1998 |
| JP | 10-268531 | | 10/1998 |
| JP | 11-212400 | | 8/1999 |
| JP | 2000-056490 | | 2/2000 |
| JP | 2000-305294 | | 11/2000 |

OTHER PUBLICATIONS

Diamond, A.S., ed. *Handbook of Imaging Materials,* Marcel Dekker, Inc., NY (1991), pp. 395-396.*
U.S. Appl. No. 60/368,253, filed Mar. 28, 2002.*
U.S. Appl. No. 60/340,041, filed Nov. 2, 2001.*
Grant, R., et al., ed., Grant & Hackh's Chemical Dictionary, fifth edition, McGraw-Hill Book Company, NY (1987), p. 80.*
U.S. Appl. No. 60/325,714, filed Sep. 28, 2001.*
U.S. Appl. No. 60/330,377, filed Oct. 18, 2001.*
U.S. Appl. No. 60/329,275, filed Oct. 12, 2001.*
U.S. Appl. No. 60/325,735, filed Sep. 28, 2001.*
U.S. Appl. No. 60/325,717, filed Sep. 28, 2001.*
U.S. Appl. No. 60/325,734, filed Sep. 28, 2001.*
U.S. Appl. No. 60/329,121, filed Oct. 12, 2001.*
U.S. Appl. No. 60/347,051, filed Jan. 8, 2002.*
Atherton, F.R., et al., "Synthesis of 3(S)-Acylamino-1-[(Phenyl)(1H-Tetrazol-5-YL) Amino]-2-2-Azetidinones," *Tetrahedron,* vol. 39, No. 15, pp. 2599-2608, 1983.
Boyd, G. V., et al., "The Dimerisation of 5-Methylene—Δ2—1-3-4-oxadiaolines" *J. Chem. Soc.*(C) vol. 12, pp. 2314-2317, 1970.
Murakami, Y., et al., "An Efficient Synthesis of 1, 1-Disubstituted Hydrazines," *Chem. & Pharmaceutical Bulletin* vol. 31, No. 2, pp. 423-428, Feb. 1983.
Chemical Abstracts, vol. 126, No. 19, May 12, 1997, Columbus, OH, USA, XP002232765.
Chemical Abstracts, vol. 133, No. 24, Dec. 11, 2000, Columbus, OH, USA, XP002232766.
Chemical Abstracts, vol. 118, No. 18, May 3, 1993, Columbus, OH, USA, XP002232767.
Chemical Abstracts, vol. 111, No. 4, Jul. 24, 1989, Columbus, OH, USA, XP002232768.
Chemical Abstracts, vol. 112, No. 8, Feb. 19, 1990, Columbus, OH, USA, XP002232769.

* cited by examiner

ELECTROPHOTOGRAPHIC ORGANOPHOTORECEPTORS WITH NOVEL CHARGE TRANSPORT COMPOUNDS

CROSS REFERENCE TO RELATED APPLICATIONS

This application claims priority to U.S. Provisional Patent Application Ser. Nos. 60/311,601, filed Aug. 10, 2001; 60/314,055, filed Aug. 22, 2001; 60/314,047, filed Aug. 22, 2001; 60/317,086, filed Sep. 4, 2001; 60/317,088, filed Sep. 4, 2001; 60/323,782, filed Sep. 20, 2001; 60/323,781, filed Sep. 20, 2001; 60/325,716, filed Sep. 28, 2001; and 60/330,381, filed Oct. 18, 2001.

FIELD OF INVENTION

This invention relates to organophotoreceptors suitable for use in electrophotography and, more specifically, to flexible organophotoreceptors having novel charge transport compounds comprising a group-substituted hydrazone.

BACKGROUND

In electrophotography, an organophotoreceptor in the form of a plate, belt, disk, or drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas (referred to as latent image). A fine liquid or solid toner is then provided in the vicinity of the latent image, and toner droplets or particles deposit in either the charged or uncharged areas to create a toned image on the surface of the photoconductive layer. The resulting visible toner image can be transferred to a suitable permanent or intermediate receiving surface such as paper, or the photoconductive layer can operate as a permanent receptor for the image. The imaging process can be repeated many times to overlay images of distinct color components or effect shadow images, such as overlaying images of distinct colors to form a full color final image.

Both single layer and multilayer photoconductive elements have been used commercially. In the single layer embodiment, a charge transport material and charge generating material are combined with a polymeric binder and then deposited on an electrically conductive substrate. In the multilayer embodiment, the charge transport material and charge generating material are present in the element in separate layers, each of which materials can optionally be combined with a polymeric binder and deposited on the electrically conductive substrate. Two arrangements are possible. In one arrangement (the "dual layer" two layer arrangement), the charge generating layer is deposited on the electrically conductive substrate and the charge transport layer is deposited on top of the charge generating layer. In an alternate arrangement (the "inverted dual layer" two layer arrangement), the order of the charge transport layer and charge generating layer is reversed.

In both the single and multilayer photoconductive elements, the purpose of the charge generating material is to generate charge carriers (i.e., holes or electrons) upon exposure to light. The purpose of the charge transport material is to accept these charge carriers and transport them through the charge transport layer in order to discharge a surface charge on the photoconductive element.

To produce high quality images, particularly after multiple cycles, it is desirable for the charge transport material to form a homogeneous solution with the polymeric binder and remain in solution. In addition, it is desirable to maximize the amount of charge which the charge transport material can accept (indicated by a parameter known as the acceptance voltage or "$V_{acc}$"), and to minimize retention of that charge upon discharge (indicated by a parameter known as the residual voltage or "$V_{res}$").

There are many charge transport materials available for electrophotography. The most common charge transport materials are pyrazoline derivatives, fluorene derivatives, oxadiazole derivatives, stilbene derivatives, hydrazone derivatives, carbazole hydrazone derivatives, triphenylamine derivatives, julolidine hydrazone derivatives, polyvinyl carbazole, polyvinyl pyrene, or polyacenaphthylene. However, each of the above charge transport materials suffers some disadvantages. There is always a need for novel charge transport materials to meet the various requirements of electrophotography applications.

SUMMARY OF THE INVENTION

An organophotoreceptor comprises a) a charge transport compound having the formula

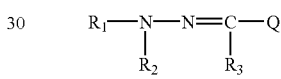

where $R_1$ and $R_2$ are selected so that $R_1$ and $R_2$ form, with the included nitrogen atom, a group selected from the group consisting of heterocyclic rings, aromatic rings, and dinaphthylamine; or $R_1$ comprises an aryl group and $R_2$ comprises a group selected from the group consisting of sulfolanyl, pyrrolyl, pyrazolyl, benzotriazolyl, stilbenyl, tetrazolyl, and the group A, wherein A is represented by the structure

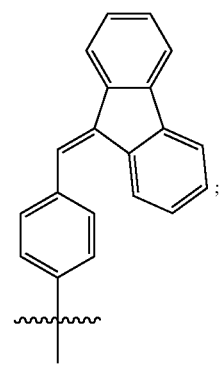

or $R_1$ comprises hydrogen, an alkyl group, or an aryl group and $R_2$ comprises sulfonylphenyl.

$R_3$ is hydrogen, an alkyl group, an aryl group, a heterocyclic group or a hydrocarbon group; and Q is a 3-carbazole group;

(b) a charge generating compound; and (c) an electrically conductive substrate.

In a fourth aspect, the invention features a novel charge transport material having the above formula.

In first embodiments, the charge transport compound has a central nucleus of the formula:

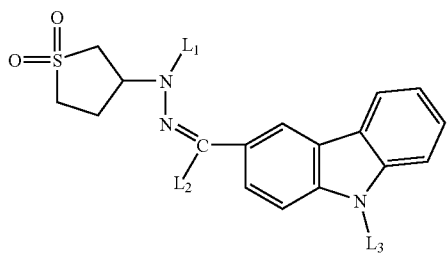

wherein $L_1$, $L_2$, and $L_3$ are independently selected from hydrogen and hydrocarbon.

In second embodiments, the charge transport compound has a central nucleus of the formula:

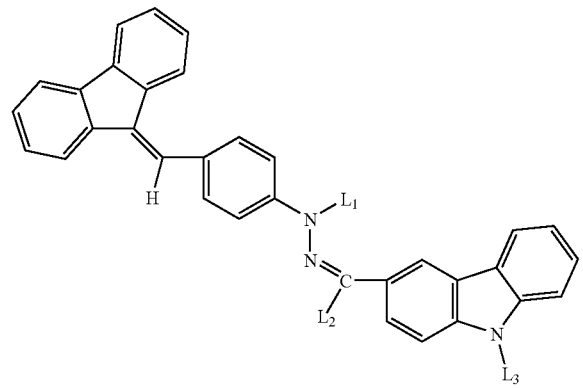

wherein $L_1$, $L_2$, and $L_3$ are independently selected from hydrogen and hydrocarbon.

In third embodiments, the charge transport compound has a central nucleus of the formula:

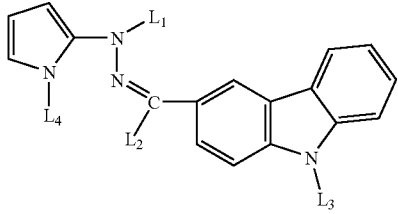

wherein $L_1$, $L_2$, and $L_3$ are independently selected from hydrogen and hydrocarbon and $L_4$ is hydrogen.

In fourth embodiments, the charge transport compound has a central nucleus of the formula:

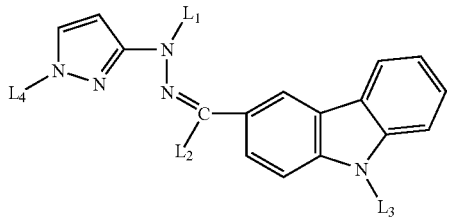

wherein $L_1$, $L_2$, and $L_3$ are independently selected from hydrogen and hydrocarbon and $L_4$ is independently selected from hydrogen and phenyl.

In fifth embodiments, the charge transport compound has a central nucleus of the formula:

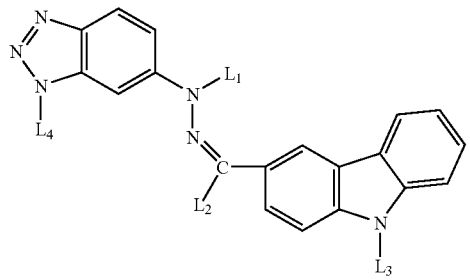

wherein $L_1$, $L_2$, and $L_3$ are independently selected from hydrogen and hydrocarbon, and $L_4$ is hydrogen.

In sixth embodiments, the charge transport compound has a central nucleus of the formula:

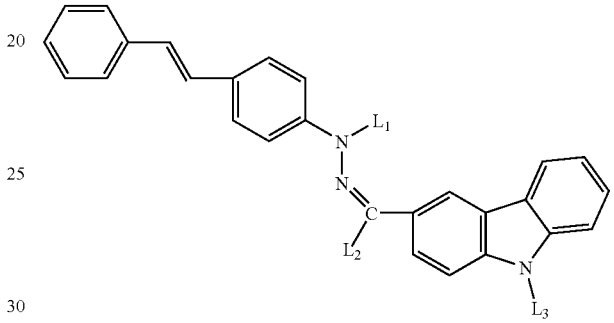

wherein $L_1$, $L_2$, and $L_3$ are independently selected from hydrogen and hydrocarbon.

In seventh embodiments, the charge transport compound has a central nucleus of the formula:

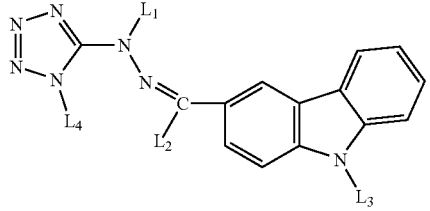

wherein $L_1$, $L_2$, and $L_3$ are independently selected from hydrogen and hydrocarbon, and $L_4$ is independently selected from hydrogen and phenylmethylene.

In eighth embodiments, the charge transport compound has a central nucleus of the formula:

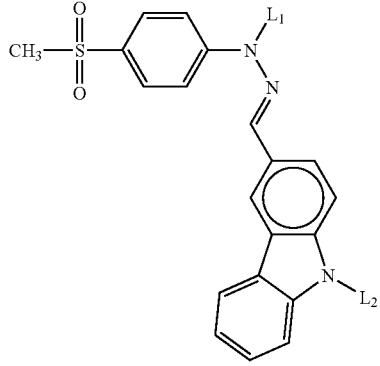

wherein $L_1$ and $L_2$ are independently selected from hydrogen and hydrocarbon.

The invention provides novel charge transport materials for organophotoreceptors featuring a combination of good mechanical and electrostatic properties. These photoreceptors can be used successfully with liquid toners to produce high quality images. The high quality of the imaging system is maintained after repeated cycling.

Other features and advantages of the invention will be apparent from the following description of the preferred embodiments thereof, and from the claims.

DETAILED DESCRIPTION OF THE INVENTION

The invention features organophotoreceptors that include novel charge transport compounds having the formula

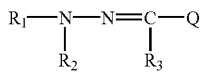

where $R_1$ and $R_2$ are selected so that $R_1$ and $R_2$ form, with the included nitrogen atom, a group selected from the group consisting of heterocyclic rings, aromatic rings, and dinaphthylamine; or $R_1$ comprises an aryl group and $R_2$ comprises a group selected from the group consisting of sulfolanyl, pyrrolyl, pyrazolyl, benzotriazolyl, stilbenyl, tetrazolyl, and the group A, wherein A is represented by the structure

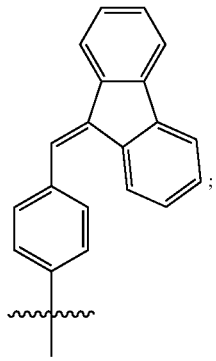

or $R_1$ comprises hydrogen, an alkyl group, or an aryl group and $R_2$ comprises sulfonylphenyl;

$R_3$ is hydrogen, an alkyl group, an aryl group, a heterocyclic group or a hydrocarbon group; and Q is a 3-carbazole group.

The variations described in groups $R_1$ and $R_2$ are a range of variations in nitrogen substitution on active compounds known in a variety of arts, such as the dye art, the photographic sensitizer art, the photoinitiator art, and the like. Rather than having a pair of distinct substituents (e.g., an alkyl groups, an aryl groups, and heterocyclic groups), there may be a single chain of a molecular entity having its alpha and omega ends bonded to the nitrogen to form a cyclic group. In particular, 5-member, 6-member and 7-member rings (with or without fused rings and substituents on the rings) are useful in the practice of the invention and are enabled by the disclosure in this application.

The charge transport compounds according to Formula (1) may be prepared by the reaction of a group-substituted hydrazine and the corresponding carbazole-3-carbaldehyde derivative in a molar ratio of 1:1 to form the corresponding hydrazone compound by refluxing the reactants in tetrahydrofuran (THF) for two hours.

The organophotoreceptor may be in the form of a plate, drum, disk, sheet, or belt, with flexible belts being preferred. The organophotoreceptor may include an electrically conductive substrate and a photoconductive element in the form of a single layer that includes both the charge transport compound and charge generating compound in a polymeric binder. Preferably, however, the organophotoreceptor includes an electrically conductive substrate and a photoconductive element that is a bilayer construction featuring a charge generating layer and a separate charge transport layer. The charge generating layer may be located intermediate or between the electrically conductive substrate and the charge transport layer. Alternatively, the photoconductive element may be an inverted construction in which the charge transport layer is located intermediate or between the electrically conductive substrate and the charge generating layer.

The electrically conductive substrate may be flexible, for example in the form of a flexible web or a belt, or inflexible, for example in the form of a drum. Typically, a flexible electrically conductive substrate comprises an insulated substrate and a thin layer of electrically conductive materials. The insulated substrate may be paper or a film forming polymer such as polyester (e.g., polyethylene terepthalate, polyethylene naphthalate), polyimide, polysulfone, polypropylene, nylon, polyester, polycarbonate, polyvinyl resin, polyvinyl fluoride, polystyrene and the like. Specific examples of supporting substrates included polyethersulfone (STABAR™ S-100, available from ICI), polyvinyl fluoride (TEDLAR™, available from E.I. DuPont de Nemours & Company), polybisphenol-A polycarbonate (MACROFOL™, available from Mobay Chemical Company) and amorphous polyethylene terephthalate (MELINAR™, available from ICI Americas, Inc.). The electrically conductive materials may be graphite, dispersed carbon black, iodide, conductive polymers such as polypyroles and CALGON® Conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide, metal coated layers, and conductive polymer coated layers. Preferably, the electrically conductive material comprises aluminum. Typically, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

In the description of chemical substituents, there are certain practices common to the art that are reflected in the use of language. Where the term 'group' is used, that term allows for the presence of further substitution on the named class of materials, as long as the substitutent is still recognizable as within the generic class. For example, where the term 'alkyl group' is used, that term would not only include unsubstituted liner, branched and cyclic alkyls, such as methyl, ethyl, isopropyl, tert-butyl, cyclohexyl, dodecyl and the like, but also substitutents such as hydroxyethyl, cyanobutyl, 1,2,3-trichloropropane, and the like. Where the term alkyl moiety is used, that term represents only an unsubstituted alkyl hydrocarbon group, whether branched, straight chain, or cyclic. Similarly, when referring to a cyclic compound by the terminology "having a central nucleus of the formula," the compound or substitutent cited will include any substitution that does not substantively alter the chemical nature of the ring groups or other salient bond structures in the formula (e.g., double bonds between nitrogens, etc.). For example, the terminology having a central nucleus of a phenyl ring would not include such alteration of the ring wherein aromaticity is removed by saturation of double bonds in the ring, while the addition of a long chain fatty acid group to replace a hydrogen atom on the phenyl ring would be included. For example, the terminology "having a central nucleus of the formula:

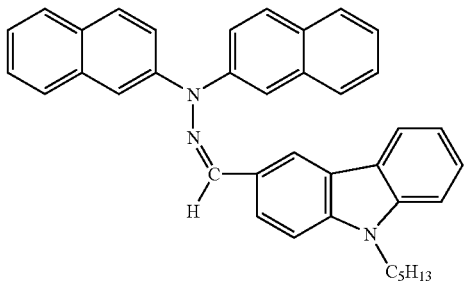

would include any compound having the cited ring structure and the defined $R_1$ (H) substituent and the defined $R_2$ ($C_5H_{13}$) substituent. The naphthyl rings may have any substituent that does not change the internal bond structure. The phenyl rings on the hydrazone likewise may have any substituent that does not alter the internal bond structure shown. The double bond between the carbon and nitrogen atom also could not be removed or converted to a single bond by additional substitution on the carbon and nitrogen atoms. This modest breadth is required as it is well known in the art to place substituents on such compounds in such positions to affect physical properties such as spectral absorbance, solubility, dispersibility, stability and the like. The disclosure is intended to enable and disclose that those rings may be so substituted, and the examples are not intended to limit the disclosure to only such unsubstituted materials. By merely providing the appropriate reagent, with substituents in the appropriate positions, the substituted final product may be provided in essentially the same chemical reaction, with only modest variations in conditions and/or solvents selected to be appropriate for those reagents and products.

Specific, non-limiting examples of suitable charge transport compounds within the general structure of the present invention have the following structures.

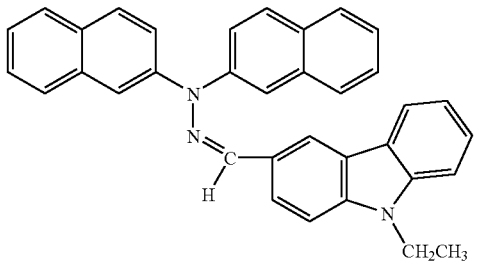

(2)

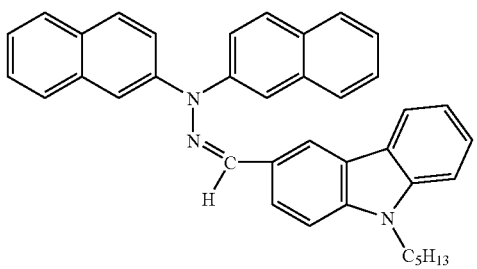

(3)

-continued

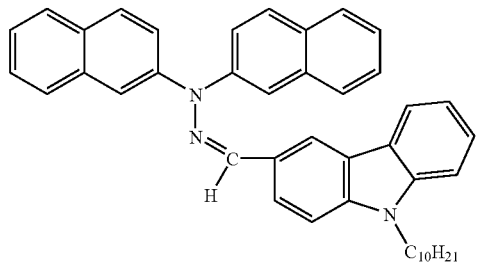

(4)

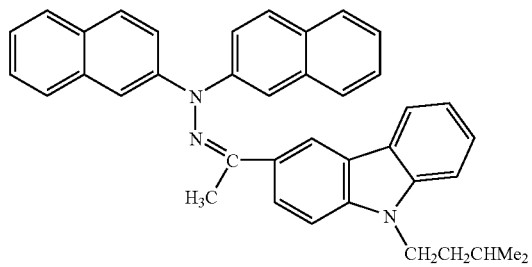

(5)

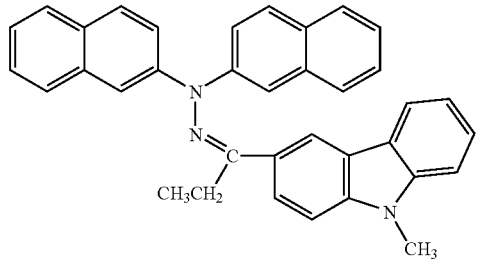

(6)

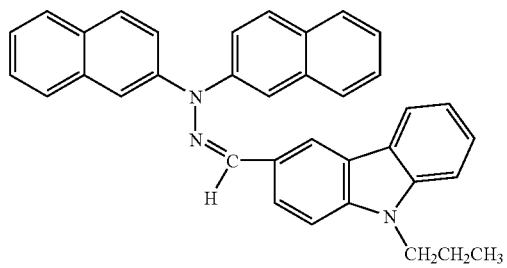

(7)

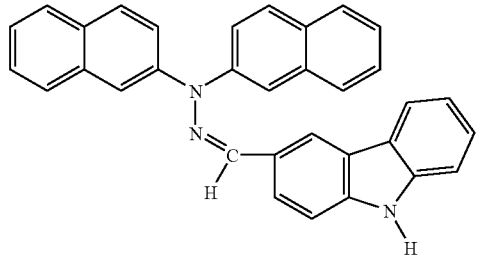

(8)

-continued
(9)
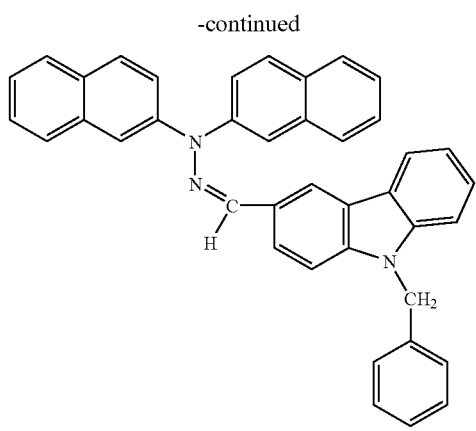
(10)
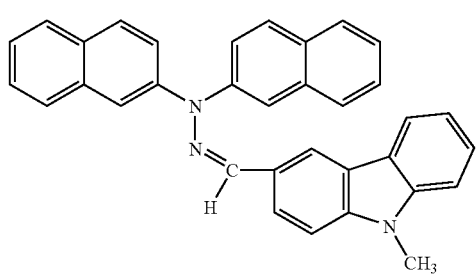
(11)
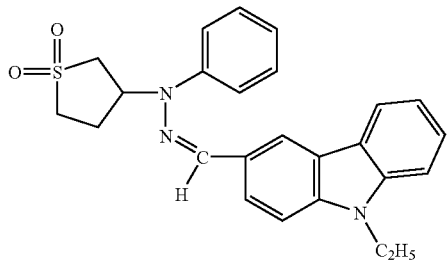
(12)
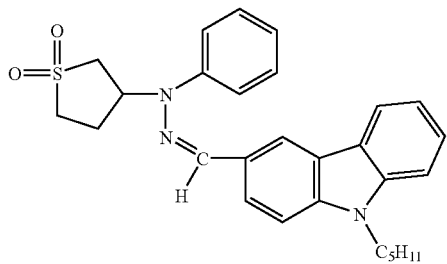
(13)
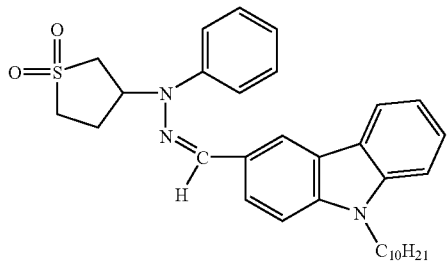
-continued
(14)
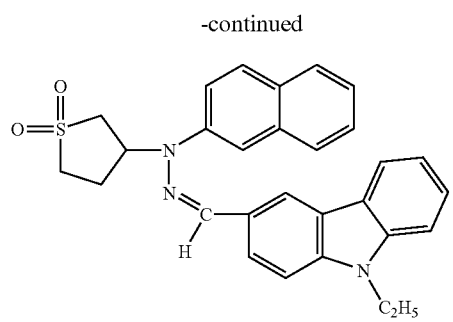
(15)
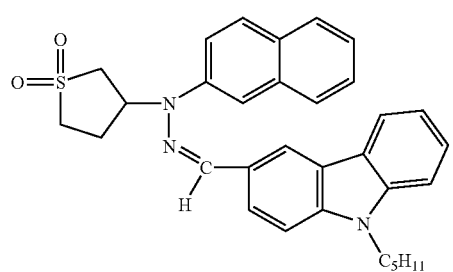
(16)
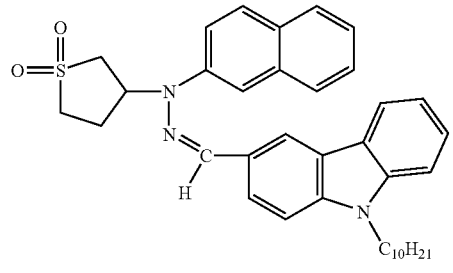
(17)
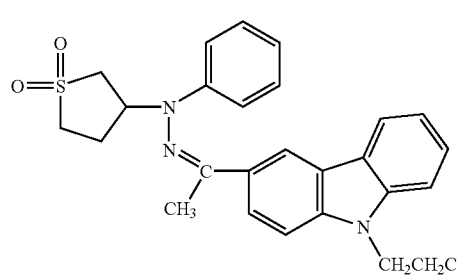
(18)
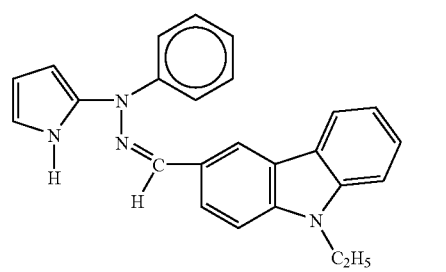

(19)
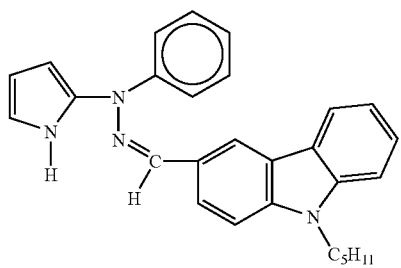
(20)
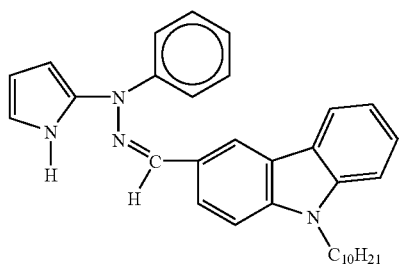
(21)
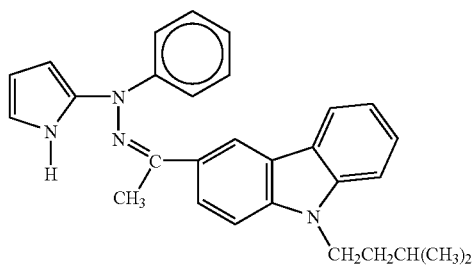
(22)
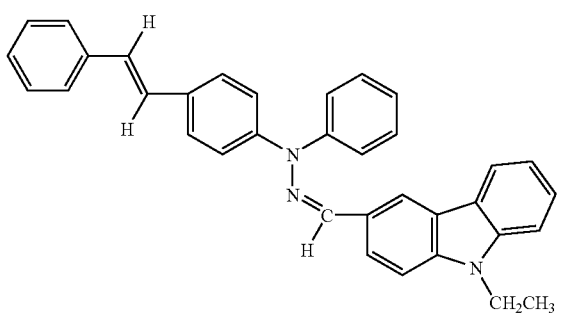
(23)
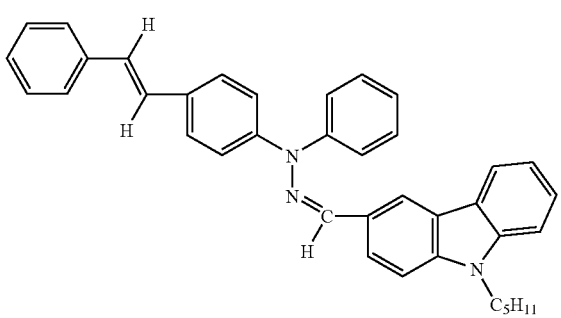
(24)
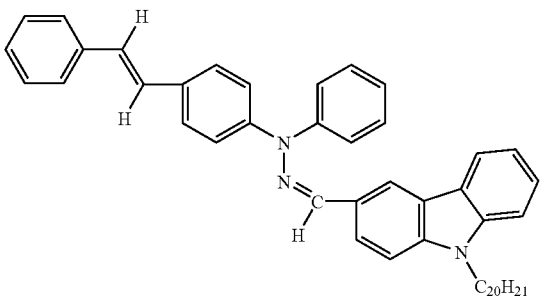
(25)
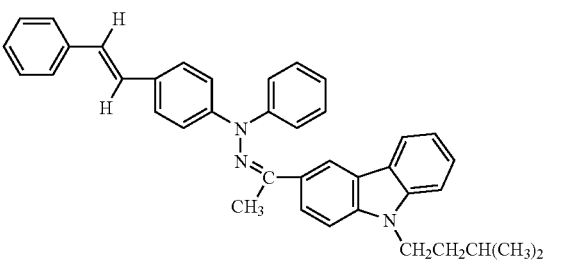
(26)
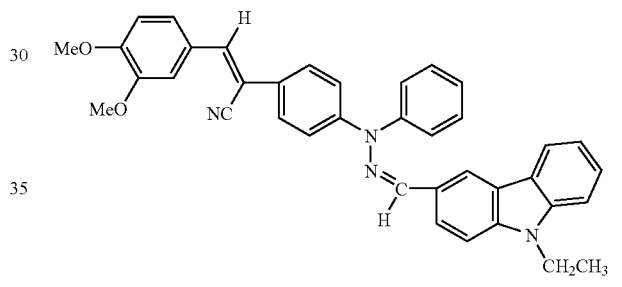
(27)
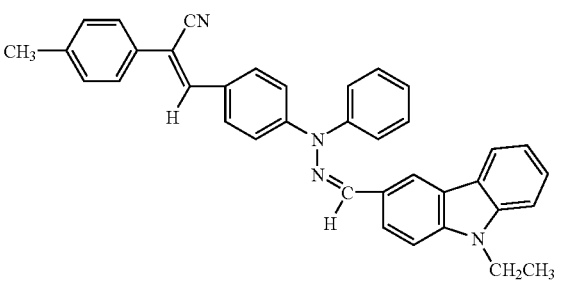
(28)
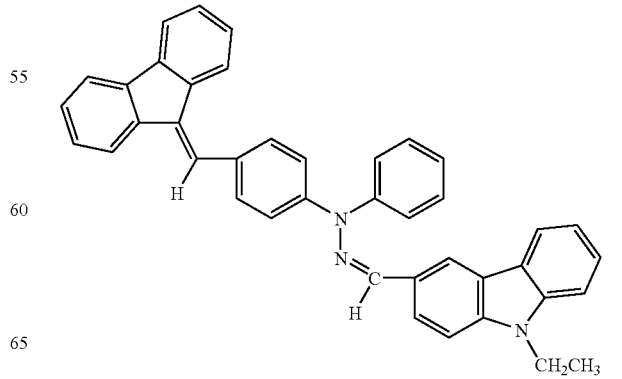

(29)
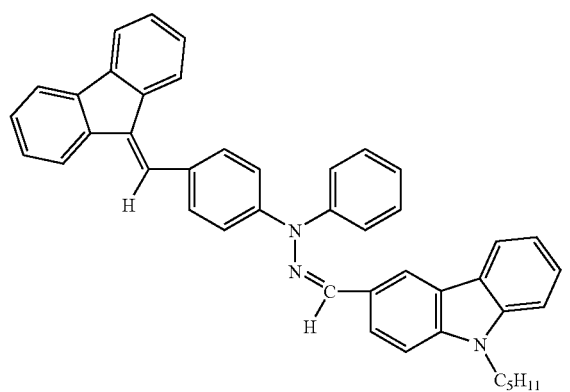
(30)
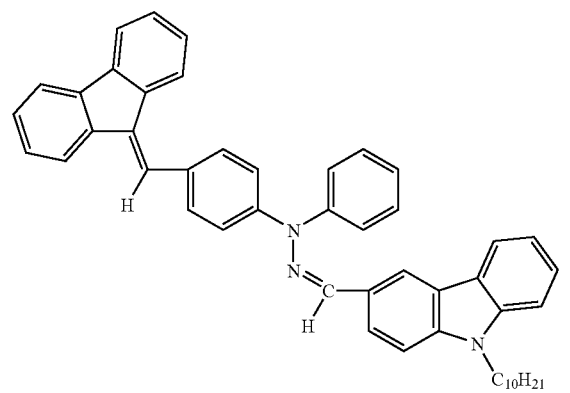
(31)
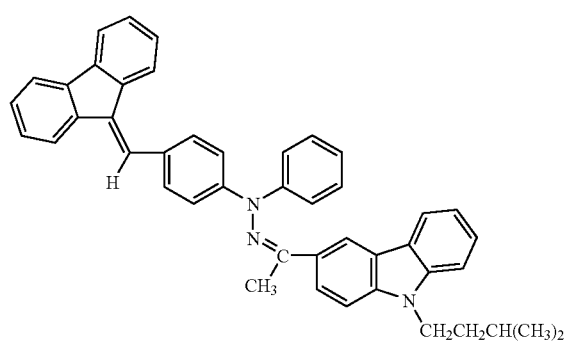
(32)
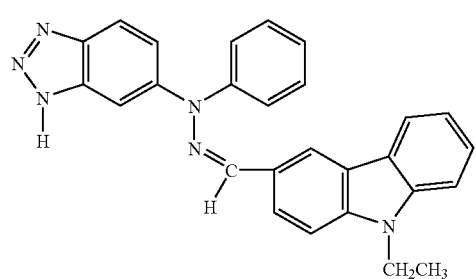
(33)
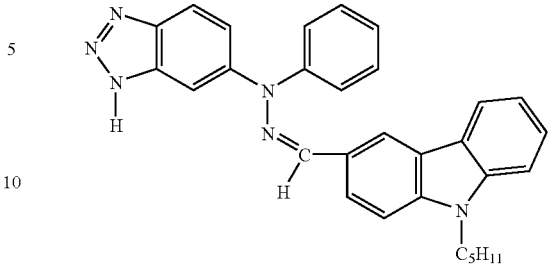
(34)
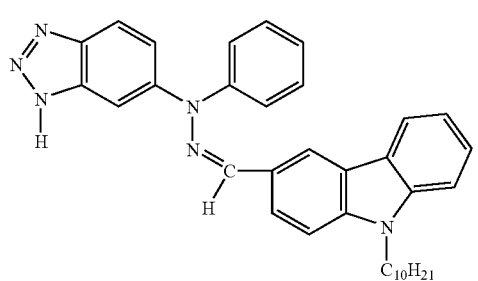
(35)
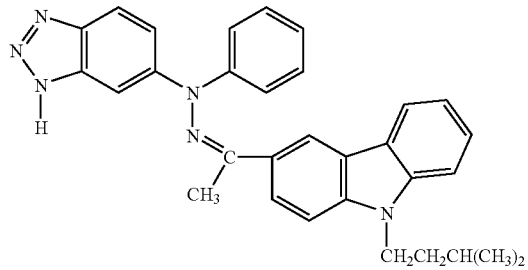
(36)
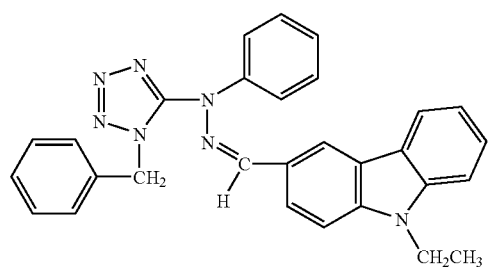
(37)
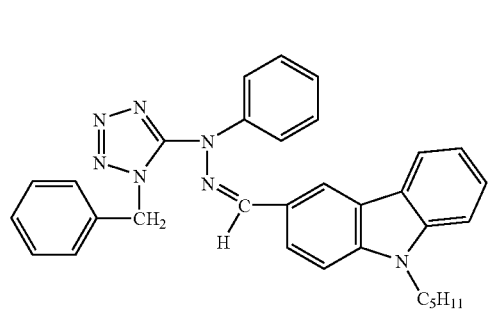

(38)
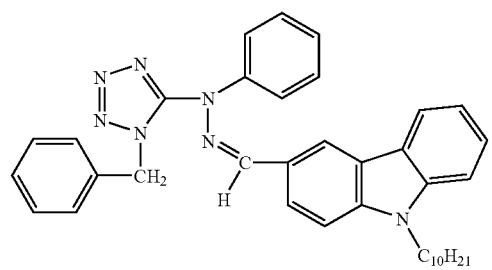
(39)
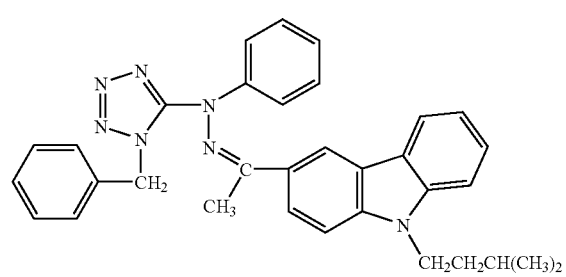
(40)
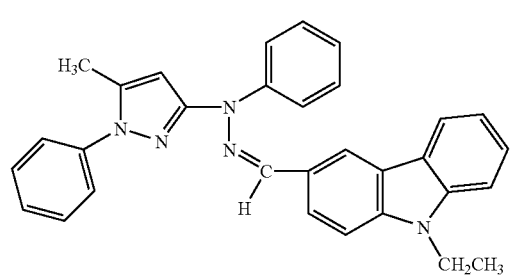
(41)
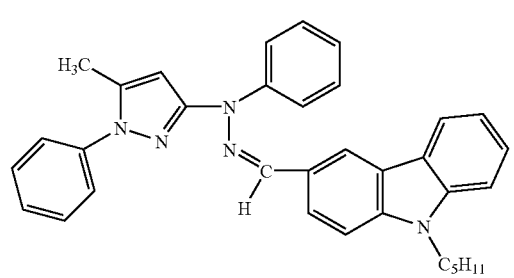
(42)
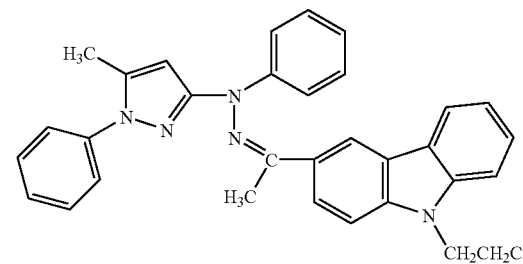
(43)
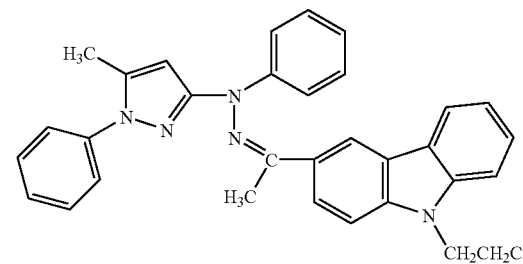
(44)
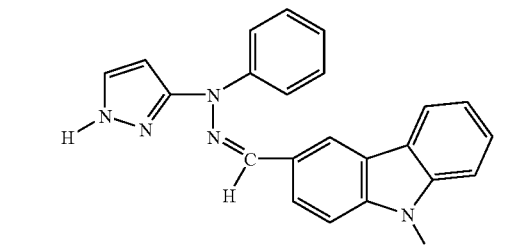
(45)
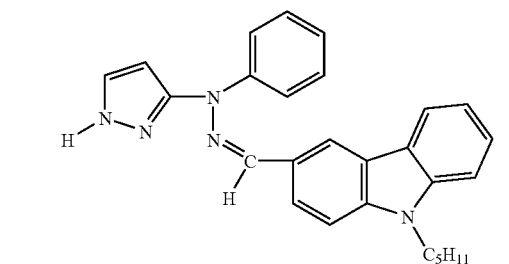
(46)
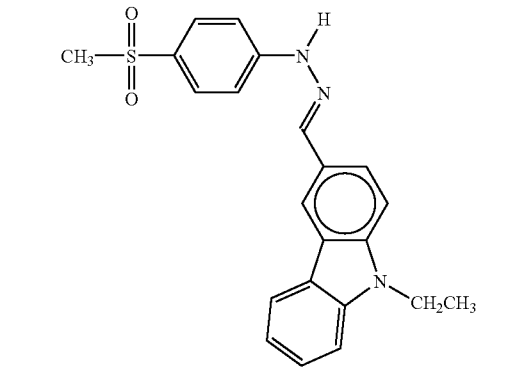
(47)
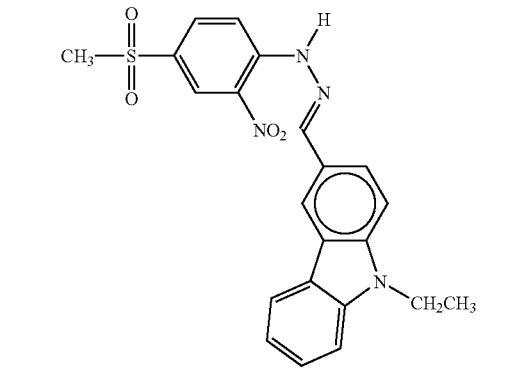

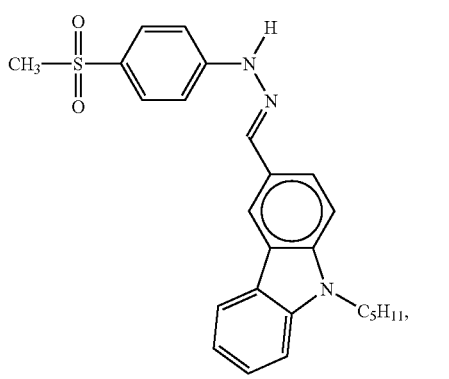

(48)

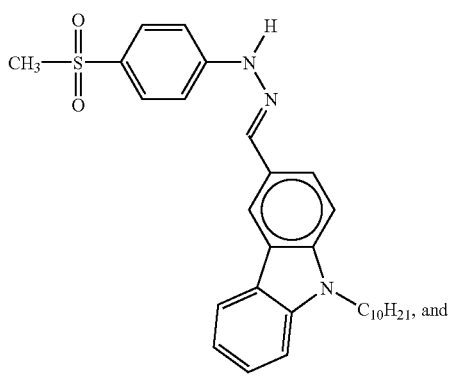

(49)

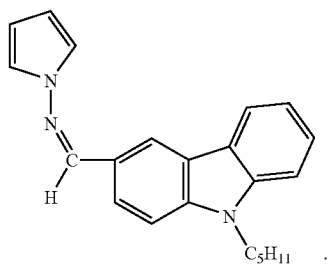

(50)

The charge generating compound is a material which is capable of absorbing light to generate charge carriers, such as a dyestuff or pigment. Non-limiting examples of suitable charge generating compounds include metal-free phthalocyanines (e.g., Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the tradename INDOFAST™ Double Scarlet, INDOFAST™ Violet Lake B, INDOFAST™ Brilliant Scarlet and INDOFAST™ Orange, quinacridones available from DuPont under the tradename MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulfoselenide, cadmiumselenide, cadmium sulfide, and mixtures thereof. Preferably, the charge generating compound is an oxytitanium phthalocyanine (e.g., any phase thereof), hydroxygallium phthalocyanine or a combination thereof.

Preferably, the charge generation layer comprises a binder in an amount of from about 10 to about 90 weight percent and more preferably in an amount of from about 20 to about 75 weight percent, based on the weight of the charge generation layer.

The binder is capable of dispersing or dissolving the charge transport compound (in the case of the charge transport layer) and the charge generating compound (in the case of the charge generating layer). Non-limiting examples of suitable binders for both the charge generating layer and charge transport layer include ethylenically unsaturated polymeric materials, such as polystyrene-co-butadiene, acrylic polymers, modified acrylic polymers, polyvinyl acetate, styrene-alkyl resins, soya-alkyl resins, polyvinylchloride, polyvinylidene chloride, polyacrylonitrile, polycarbonates, polyacrylic acid, polyacrylates, polymethacrylates, styrene polymers, polyvinyl acetals (e.g., polyvinyl butyral), alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Polycarbonate binders are particularly preferred. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates.

The photoreceptor may include additional layers as well. Such layers are well-known and include, for example, barrier layers, release layers, adhesive layer, and sub-layer. The release layer forms the uppermost layer of the photoconductor element with the barrier layer sandwiched between the release layer and the photoconductive element. The adhesive layer locates and improves the adhesion between the barrier layer and the release layer. The sub-layer is a charge blocking layer and locates between the electrically conductive substrate and the photoconductive element. The sub-layer may also improve the adhesion between the electrically conductive substrate and the photoconductive element.

Suitable barrier layers, where desired, include coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above organic binders optionally may contain small inorganic particles such as fumed silica, silica, titania, alumina, zirconia, or a combination thereof. The typical particle size is in the range of 0.001 to 0.5 micrometers, preferably 0.005 micrometers. A preferred barrier layer is a 1:1 mixture of methyl cellulose and methyl vinyl ether/maleic anhydride copolymer with glyoxal as a crosslinker.

The release layer topcoat may comprise any release layer composition known in the art. Preferably, the release layer is a fluorinated polymer, siloxane polymer, fluorosilicone polymer, silane, polyethylene, polypropylene, polyacrylate, or a combination thereof. More preferably, the release layers are crosslinked silicone polymers.

Typical non-limiting examples of adhesive layers include film forming polymers such as polyester, polyvinylbutyral, polyvinylpyrolidone, polyurethane, polymethyl methacrylate, poly(hydroxy amino ether) and the like. Preferably, the adhesive layer is poly(hydroxy amino ether). If such layers are utilized, they preferably have a dry thickness between about 0.01 micrometer and about 5 micrometers.

Typical non-limiting examples of sub-layers include polyvinylbutyral, organosilanes, hydrolyzable silanes, epoxy resins, polyesters, polyamides, polyurethanes, silicones and the like. Preferably, the sub-layer has a dry thickness between about 20 Angstroms and about 2,000 Angstroms.

The charge transport compounds, and photoreceptors including these compounds, are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The invention will now be described further by way of the following examples.

EXAMPLES

I. Synthetic Background

Examples of the synthesis of the subgeneric groups hydrazones of the present invention are provided below. Although the examples are separated by synthesis, the preparation of intermediates and the actual synthetic steps are similar, showing the generic nature of the characterization of these hydrazones. For the most part, the structures differ with regard to the nature of the ring group (heterocyclic, aromatic, or blended) shown in the $R_2$ position in the generic formula (I) shown for the class of compounds of the invention.

All of the hydrazones fall within the generic definitions of a charge transport compound having the formula

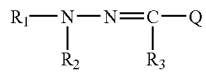

where $R_1$ and $R_2$ are selected so that $R_1$ and $R_2$ form, with the included nitrogen atom, a group selected from the group consisting of dinaphthylamine; or $R_1$ comprises an aryl group and $R_2$ comprises a group selected from the group consisting of sulfolanyl, pyrrolyl, pyrazolyl, benzotriazolyl, stilbenyl, tetrazolyl, and group A, wherein group A is represented by the structure

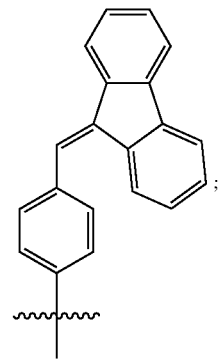

$R_1$ comprises hydrogen, an alkyl group, or an aryl group and $R_2$ comprises sulfonylphenyl.

$R_3$ is hydrogen, an alkyl group, aryl group, a heterocyclic group or a hydrocarbon group; and Q is a 3-carbazole group.

A. Synthesis Relating to DiNaphthalene Hydrazones 1,1-Dinaphthylhydrazine 1,1-Dinaphthylhydrazine can be prepared according to the procedure described in *Journal of the General Chemistry* (1964), 34, 136 by Staschkow et el., which is incorporated herein by reference.

A suspension of 0.07 mole of the naphthyl nitrosamine in 750 ml of ether was cooled to 5-8° C. and treated with 150 g of zinc dust. 70 ml of acetic acid was then added drop wise with stirring. To complete the reaction, 40 g of zinc dust was added. The reaction mixture was heated and filtered from the sludge. The mother liquor was washed with 10% sodium carbonate solution and dried with solid KOH. The ether was distilled off to give the crystalline hydrazines, which was crystallized from ethanol or butanol.

Compound (2)

9-Ethyl-3-carbazolecarboxaldehyde (2.23 g, 0.01 mole, commercially available from Aldrich, Milwaukee, Wis.) and 1,1-Dinaphthylhydrazine (2.86 g, 0.01 mole) in a molar ratio of 1:1 is refluxed in tetrahydrofuran (20 ml) for 16 hours with stirring. Upon removal of the solvent, the crude Compound (2) is isolated and purified by recrystallization.

Compound (3)

Compound (3) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried (MgSO$_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-penthyl-3-carbazolecarboxaldehyde.

9-Penthyl-3-carbazolecarboxaldehyde or N-Pentyl-3-formyl carbazole (2.65 g, 0.01 mole) and 1,1-Dinaphthylhydrazine (2.86 g, 0.01 mole) in a molar ratio of 1:1 is refluxed in tetrahydrofuran (20 ml) for 16 hours with stirring. Upon removal of the solvent, the crude Compound (3) is isolated and purified by recrystallization.

Compound (4)

Compound (4) can be prepared by the procedure for Compound (3) except 0.1 mole of 1-bromopentane is replaced with 0.1 mole of 1-bromodecane (commercially available from Aldrich, Milwaukee, Wis.).

Compound (5)

Compound (5) can be prepared by the procedure for Compound (2) except 0.01 mole of 9-Ethyl-3-carbazolecarboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

Compound (6)

Compound (6) can be prepared by the procedure for Compound (2) except 0.01 mole of 9-Ethyl-3-carbazolecarboxaldehyde is replaced with 0.01 mole of 1-(9-methyl-9H-carbazol-3-yl)-1-propanone (commercially available from Interbioscreen Ltd., P.O. Box 218, Moscow 121019, Russia; web: www.ibscreen.com).

Compound (7)

Compound (7) can be prepared by the procedure for Compound (2) except 0.01 mole of 9-Ethyl-3-carbazolecarboxaldehyde is replaced with 0.01 mole of 9-propyl-carbazole-3-carboxaldehyde (commercially available from AsInEx, 6 Schukinskaya Street, Moscow 123182, Russia; web: www.asinex.com).

Compound (8)

Compound (8) can be prepared by the procedure for Compound (2) except 0.01 mole of 9-Ethyl-3-carbazolecarboxaldehyde is replaced with 0.01 mole of 9-H-carbazole-3-carboxaldehyde (commercially available from TimTec, Inc., Wilmington, Del.; web: www.timtec.net).

Compound (9)

Compound (9) can be prepared by the procedure for Compound (2) except 0.01 mole of 9-Ethyl-3-carbazolecarboxaldehyde is replaced with 0.01 mole of 9-(phenylmethyl)-carbazole-3-carboxaldehyde (commercially available from AsInEx, 6 Schukinskaya Street, Moscow 123182, Russia; web: www.asinex.com).

Compound (10)

Compound (10) can be prepared by the procedure for Compound (2) except 0.01 mole of 9-Ethyl-3-carbazolecarboxaldehyde is replaced with 0.01 mole of 9-methyl-carbazole-3-carboxaldehyde (commercially available from TimTec, Inc., Wilmington, Del.; web: www.timtec.net).

II. Organophotoreceptor Preparation Methods

Inverted dual layer organophotoreceptor can be prepared by incorporating Compounds (2)-(50). A charge transport solution containing 50 wt. % of one the compounds in Polycarbonate Z binder can be prepared by combining a solution of 1.25 g of the compound in 8.0 g of tetrahydrofuran with 1.25 g of Polycarbonate Z in 2.50 g of toluene. The charge transport solution is then knife-coated onto a 3 mil (76 micrometer) thick aluminized polyethylene terephthalate film (MELINEX™ 442 polyester film from Dupont having a 1 ohm/square aluminum vapor coat) having a 0.3 micron polyester resin sub-layer (Vitel® PE-2200 from Bostik, Middletown, Mass.) and dried to form a charge transport layer having a thickness of 9 micrometers.

A dispersion can be prepared by micronising 1.35 g of oxytitanium phthalocyanine pigment (H. W. Sands Corp., Jupiter, Fla.), 1.35 g of S-Lec B Bx-5 polyvinylbutryal resin (Sekisui Chemical Co. Ltd.), 26 g of methyl ethyl ketone, and 13 g of toluene using a horizontal sand mill operating in recirculation mode for 8 hours. The resulting dispersion is then knife-coated onto the charge transport layer and dried at 80° C. for 10 minutes to form a charge generating layer having a thickness of 0.27 micrometer on the PET film.

III. Electrostatic Testing

Electrostatic testing of the inverted dual layer organophotoreceptors prepared from the compounds can be performed and recorded on a QEA PDT-2000 instrument at ambient temperature. Charge-up is performed at 8 kV. Discharge is performed by exposing the photoreceptor to a 780 nm-filtered tungsten light source down a fiber optic cable. Each sample is exposed to 2 microjoules/cm$^2$ of energy for 0.05 seconds; the total exposure intensity is 20 microwatts/cm$^2$. After charge-up, the acceptance voltage ($V_{acc}$) is measured in volts. This value is recorded as $V_{acc}$ after one cycle. Following this initial charge-up, a one second dark decay followed before the sample is discharged with the 0.05 second light pulse of 2 microjoules/cm$^2$ at 780 nm, one second after which the decrease in voltage (Contrast) is measured in volts. Then the charge on the sample is further reduced by an eraser lamp. The final residual voltage ($V_{res}$) on the sample is measured in volts. $V_{acc}$ and $V_{res}$ are also measured after a total of 1000 cycles. In general, it is desirable to maximize $V_{acc}$ and to minimize $V_{res}$.

SUPPLEMENTAL EXAMPLES

Preparation of N-Phenyl-N-sulfolan-3-ylhydrazine

The compound has been synthesized according to the following procedure

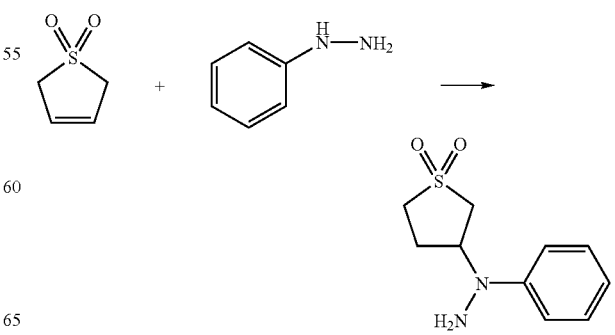

Butadiene sulfone (0.5 mol, obtained from Aldrich chemicals, Milwaukee, Wis.) and phenyl hydrazine (0.55 mol, 1.1 equiv. obtained from Aldrich Chemicals, Milwaukee, Wis.) were stirred for 5-10 minutes, and then 40% aqueous KOH solution (0.005 mol, 0.01 equiv. obtained from Aldrich Chemicals, Milwaukee, Wis.)) was added. The mixture was heated at 60° C. for 2 hours whereupon a solid separated. After 10 hours at room temperature, the solid was filtered, washed with excess of water and recrystallized from methanol to give the product as white crystals; yield 53%; mp 119.9-121.5° C.; $^1$H-NMR and $^{13}$C-NMR spectra in CDCl$_3$ were in full agreement with the structure.

Preparation of 1-Aminopyrrole

1-Aminopyrrole was synthesized in two steps from the N-aminophthalamide (1) according to the following scheme.

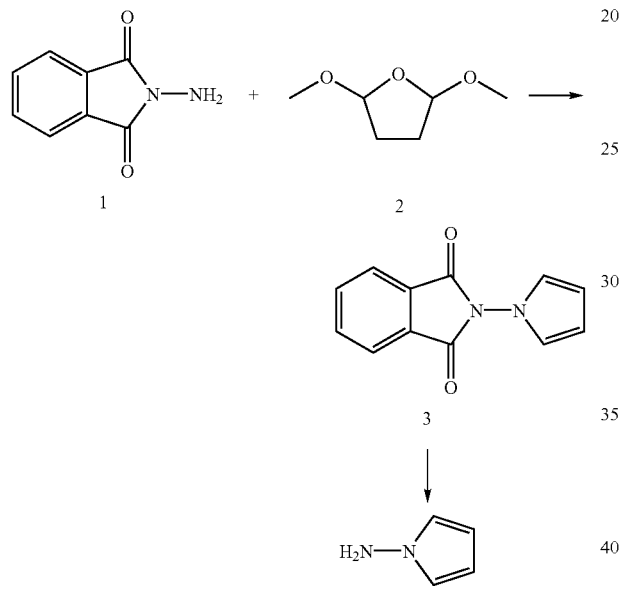

Step one:—Preparation of 2-(1H-pyrrol-1-yl)-1H-isoindole-1,3(2H)-dione:—N-aminophthalamide (1, 10 g, 62 mmol; obtained from Aldrich Chemicals; Milwaukee, Wis.) and 1,5-dimethoxytetrahydrofuran (2, 12 mL, 90 mmol; obtained from Aldrich Chemicals; Milwaukee, Wis.) were refluxed in 100 mL of dry 1,4-dioxane for few minutes to form a clear yellow solution. 5 N HCl (10 mL) was then added and stirred. White precipitate started to appear after 15-20 minutes. This solution with precipitate was allowed to stir for another 1 hour and was then cooled in an ice-water bath. The precipitate formed were filtered and washed with 150 mL of dioxane/water (⅓), and dried in air to give 3 as yellow prisms; yield 78%; mp 219-220° C.; $^1$H-NMR and $^{13}$C-NMR were in full agreement with the structure.

Step two:—Preparation of 1-aminopyrrole:—To a suspension of 3 (103 g, 0.5 mol) in 500 mL methanol, 30 mL of hydrazine hydrate (88%, w/v, obtained from Aldrich Chemicals, Milwaukee; Wis.) was added. The suspension disappeared and the resulting solution was heated to reflux. White solid was formed from the clear solution. After 45 minutes of heating under reflux, the reaction mixture was cooled to room temperature, and 15 mL of acetic acid was added and stirred. The solid obtained was filtered off and washed with methanol. The filtrate was collected and concentrated to give white residue to which NaOH (2M, 100 mL) was added to dissolve. This mixture was extracted with ether, dried over MgSO$_4$, and concentrated to give a product as yellow oil; yield 40%; $^1$H-NMR and $^{13}$C-NMR spectra were in full agreement with the structure of the compound.

4-Methylsulfonylphenylhydrazine hydrochloride

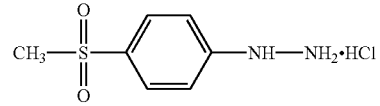

Commercially available from Fisher Scientific USA, Pittsburgh, Pa.

1,1'-(sulfonyldi-4-1-Phenylene)bis-hydrazine

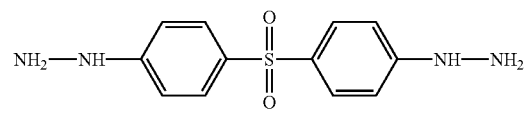

Commercially available from Vistas-M (Moscow, Russia)

Preparation of N-Pentyl-3-formyl Carbazole

This material was prepared according to the following procedure

Step one:—Preparation of N-Pentylcarbazole:—To a 1 liter 3-neck round bottom flask equipped with reflux condenser and mechanical stirrer were added 250 g carbazole (1.5 mol; obtained from Aldrich Chemicals; Milwaukee; Wis.), 241.7 g 1-bromopentane (1.6 mol; obtained from Aldrich Chemicals; Milwaukee; Wis.), 17 g benzyltriethyl ammonium chloride (0.075 mol; obtained from Aldrich Chemicals; Milwaukee; Wis.) and 1000 ml of toluene. The mixture was stirred at room temperature for 0.5 hr., followed by the addition of an aqueous solution of NaOH (prepared by dissolving 300 g of NaOH in 300 g water). The mixture was refluxed for 5 hours and cooled to room temperature. The organic phase was separated and washed repeatedly with water until the pH of the washing water was neutral. The organic phase was dried over $Mg_2SO_4$, filtered, and evaporated to dryness to obtain 345 g of brown liquid (97% yield). $^1$H-NMR and IR spectra were in agreement with the structure of N-heptylcarbazole. H-NMR spectrum in CDCl3 was also in full agreement with the structure.

Step two:—preparation of N-Pentyl-3-formylcarbazole: To a 1-liter, 3-neck round bottom flask (RBF) equipped with mechanical stirrer, thermometer, and addition funnel, was added 600 ml DMF. The contents were cooled in a salt/ice bath. When the temperature inside the flask reached 0° C., 154 ml of $POCl_3$ (1.65 mol; obtained from Aldrich Chemicals; Milwaukee; Wis.) was slowly added. During the addition of $POCl_3$, the temperature inside the flask was not allowed to rise above 5° C. After the addition of $POCl_3$ was completed, the reaction mixture was allowed to warm to room temperature. 345 g of N-heptylcarbazole (1.50 mole; prepared in step one) was then added and the flask was heated to 90° C. for 2 hours using a heating mantle. The reaction mixture was cooled to room temperature and the solution was added slowly to a 4.5 liter beaker containing a solution of 820 g sodium acetate dissolved in 2 liters of water. The beaker was cooled in an ice bath and stirred for 3 hr. The brownish solid obtained was filtered and washed repeatedly with water, followed by a small amount of ethanol (50 ml). The resulting product was recrystallized once from toluene using activated charcoal and dried under vacuum in an oven heated at 70° C. for 6 hours to obtain 330 g (83% yield) of N-heptyl-3-diformyl-carbazole. $^1$H-NMR spectra confirmed the presence of N-heptyl-3-diformyl-carbazole.

B. Synthesis Relating to the Sulfolanyl Hydrazones

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (I) (93%) having a melting point of 119-20° C. (MeOH).

N-(2-Naphthyl)-N-sulfolan-3-ylhydrazine

N-(2-Naphthyl)-N-sulfolan-3-ylhydrazine can be prepared according to the procedure for N-phenyl-N-sulfolan-3-ylhydrazine except phenylhydrazine is replaced with 2-naphthylhydrazine. 2-Naphthylhydrazine can be prepared according to the procedure described in Chinese Patent No. 1,175,571 by Su et al., which is incorporated herein by reference. 2-Naphthylhydrazine can also be prepared by neutralizing 2-naphthylhydrazine hydrochloride with potassium hydroxide, which is commercially available from Apin Chemical Ltd. (UK), 82C Milton Park, Abingdon, Oxon, OX14 4RY, United Kingdom. (Web: http://www.apinchemicals.com.)

To a mixture of 0.5 mole of butadiene sulfone (commercially available from Aldrich, Milwaukee, Wis.) and 0.55 mole of 2-naphthylhydrazine is added 0.005 mole 40% aqueous potassium hydroxide solution. The mixture is kept for 16 hours at 60° C. N-(2-Naphthyl)-N-sulfolan-3-ylhydrazine is isolated and purified.

Synthesis of N-Phenyl-N-sulfolan-3-ylhydrazone of 9-Ethyl-3-carbazolecarboxaldehyde (Compound 11)

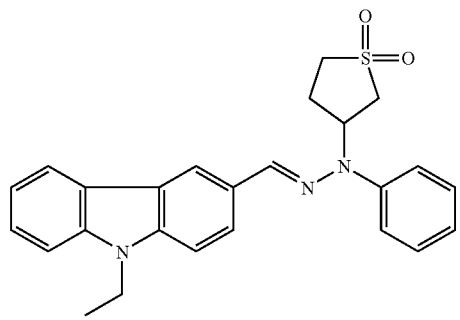

Compound (11)

To a 500 ml 3-neck RBF equipped with reflux condenser and mechanical stirrer, were added 22.32 g of 9-Ethyl-3-Carbazolecarboxaldehyde (0.1 mole, obtained from Aldrich Chemical Co., P.O. Box 2060, Milwaukee, Wis. 53201 and used as received) and 24.86 g of N-phenyl-N-sulfolan-3-ylhydrazine (0.11 mole, as prepared in experimental section (A) in 300 ml of toluene in the presence to 5 drops of concentrated sulfuric acid. The solution was refluxed for 2 hours. TLC (Thin layer chromatography) showed the disappearance of the starting materials and the appearance of the product. The solution was cooled to room temperature, and then decanted to remove a very small amount of dark solid at the bottom of the flask. The toluene solution was extracted several times with 100 ml of water until the pH of the water was neutral. The toluene solution was dried over magnesium sulfate and evaporated until approximately 100 ml remained and was then cooled in an ice bath to precipitate the product which was collected and dried and recrystalyzed 3 times from toluene with activated charcoal. In the third recrystalyzation, we used also silica gel in addition to the activated charcoal. Obtained: H-NMR spectrum in CDCl3 in agreement with the structure Synthesis of Compound 12,
N-Phenyl-N-sulfolan-3-ylhydrazone of
9-Pentyl-3-carbazolecarboxaldehyde

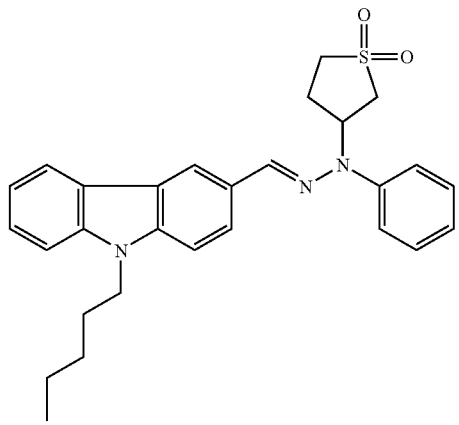

Compound (12)

To a 500 ml 3-neck RBF equipped with reflux condenser and mechanical stirrer, were added 22.32 g of 9-Pentyl-3-Carbazolecarboxaldehyde (0.1 mole, Prepared as in experimental section (B)) and 24.86 g of N-phenyl-N-sulfolan-3-ylhydrazine (0.11 mole) (prepared in section (A)) in 300 ml of toluene in the presence to 5 drops of concentrated Sulfuric acid. The solution was refluxed for 2 hours. TLC showed the disappearance of the starting materials and the appearance of the product. The solution was cooled to room temperature, decanted to remove a very small amount of dark solid at the bottom of the flask. The toluene solution was extracted several times with 100 ml of water until the pH of the water was neutral. The toluene solution was dried over magnesium sulfate and evaporated till dryness. Obtained was a gummy liquid which solidified upon standing at RT. The product was collected and dried and recrystalyzed 3 times from Toluene with activated charcoal. In the third recrystalyzation, we used also silica gel in addition to the activated charcoal. Obtained: H-NMR spectrum in CDCl3 in agreement with the structure Compound (13)

Compound (13) can be prepared by the procedure for Compound (12) except 0.1 mole of 1-bromopentane is replaced with 0.1 mole of 1-bromodecane (commercially available from Aldrich, Milwaukee, Wis.).

Compound (14)

9-Ethyl-3-carbazolecarboxaldehyde (2.23 g, 0.01 mole, commercially available from Aldrich, Milwaukee, Wis.) and N-(2-naphthyl)-N-sulfolan-3-ylhydrazine (2.76 g, 0.01 mole) is refluxed in tetrahydrofuran (20 ml) for 16 hours with stirring. Upon removal of the solvent, the crude Compound (14) is isolated and purified by recrystallization.

Compound (15)

Compound (15) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried ($MgSO_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazole-carboxaldehyde.

9-Pentyl-3-carbazolecarboxaldehyde (2.65 g, 0.01 mole, commercially available from Aldrich, Milwaukee, Wis.) and N-(2-naphthyl)-N-sulfolan-3-ylhydrazine (2.76 g, 0.01 mole) is refluxed in tetrahydrofuran (20 ml) for 16 hours with stirring. Upon removal of the solvent, the crude Compound (15) is isolated and purified by recrystallization.

Compound (16)

Compound (16) can be prepared by the procedure for Compound (15) except 0.1 mole of 1-bromopentane is replaced with 0.1 mole of 1-bromodecane (commercially available from Aldrich Chemicals, Milwaukee, Wis.).

Compound (17)

Compound (17) can be prepared by the procedure for Compound (11) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

C. Synthesis Relating to the Carbazole Pyrrolyl Hydrazones

N-Pyrrol-2-yl-N-phenylhydrazine

N-Pyrrol-2-yl-N-phenylhydrazine can be prepared according to the procedure described in Japanese Patent No. 05148210 by Myamoto, which is incorporated herein by reference.

Compound (18)

9-Ethyl-3-carbazolecarboxaldehyde (2.23 g, 0.01 mole, commercially available from Aldrich, Milwaukee, Wis.) and N-pyrrol-2-yl-N-phenylhydrazine (1.73 g, 0.01 mole) is refluxed in tetrahydrofuran (20 ml) for 16 hours with stirring. Upon removal of the solvent, the crude Compound (18) is isolated and purified by recrystallization.

Compound (19)

Compound (19) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried ($MgSO_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazole-carboxaldehyde.

9-Pentyl-3-carbazolecarboxaldehyde (2.65 g, 0.01 mole, commercially available from Aldrich, Milwaukee, Wis.) and N-pyrrol-2-yl-N-phenylhydrazine (1.73 g, 0.01 mole) is refluxed in tetrahydrofuran (20 ml) for 16 hours with stirring. Upon removal of the solvent, the crude Compound (19) is isolated and purified by recrystallization.

Compound (20)

Compound (20) can be prepared by the procedure for Compound (19) except 0.1 mole of 1-bromopentane is replaced with 0.1 mole of 1-bromodecane (commercially available from Aldrich, Milwaukee, Wis.).

Compound (21)

Compound (21) can be prepared by the procedure for Compound (19) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

D. Synthesis Relating to Carbazole N-stilbenyl-N-phenylhydrazones

N-(4-Stilbenyl)-N-phenylhydrazine

N-(4-Stilbenyl)-N-phenylhydrazine can be prepared according to the procedure described in Zh. Org. Khim.

(1967), 3(9), 1605-3 by Matevosyan et el., which is incorporated herein by reference. To a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif.; Web: www.spectrumchemical.com) heated to boiling temperature, sodium was slowly added until there was no more discharge of red coloration. After boiling for some time the mixture was dissolved in 1750 ml of ethanol and cooled to −15° C. The precipitated product was recrystallized to give 28% of N-(4-stilbenyl)-N-phenylhydrazine.

Compound (22)

9-Ethyl-3-carbazolecarboxaldehyde (2.23 g, 0.01 mole, commercially available from Aldrich, Milwaukee, Wis.) and N-(4-stilbenyl)-N-phenylhydrazine (2.86 g, 0.01 mole) is refluxed in tetrahydrofuran (20 ml) for 16 hours with stirring. Upon removal of the solvent, the crude Compound (22) is isolated and purified by recrystallization.

Compound (23)

Compound (23) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried (MgSO$_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazolecarboxaldehyde.

9-Pentyl-3-carbazolecarboxaldehyde (2.65 g, 0.01 mole, commercially available from Aldrich, Milwaukee, Wis.) and N-(4-stilbenyl)-N-phenylhydrazine (2.86 g, 0.01 mole) is refluxed in tetrahydrofuran (20 ml) for 16 hours with stirring. Upon removal of the solvent, the crude Compound (23) is isolated and purified by recrystallization.

Compound (24)

Compound (24) can be prepared by the procedure for Compound (23) except 0.1 mole of 1-bromopentane is replaced with 0.1 mole of 1-bromodecane (commercially available from Aldrich, Milwaukee, Wis.).

Compound (25)

Compound (25) can be prepared by the procedure for Compound (22) except 0.01 mole of 9-Ethyl-3-carbazolecarboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

Compound (26)

Compound (26) can be prepared according to the following procedure. To a mixture of phenylhydrazine (19.4 g, 0.18 mole, commercially available from Aldrich, Milwaukee, Wis.) and alpha-(4-chlorophenyl)-3,4-dimethoxycinnamonitrile (6.00 g, 0.02 mole, CAS # 65952-64-9; commercially available from Aldrich, Milwaukee, Wis.) heated to boiling temperature, sodium was slowly added until there was no more discharge of red coloration. After boiling for some time the mixture was dissolved in 350 ml of ethanol and cooled to −15° C. The precipitated product was recrystallized to give N-(3,4-dimethoxycinnamonitrile-alpha-phenyl)-N-phenylhydrazine. 9-Ethyl-3-carbazolecarboxaldehyde (2.23 g, 0.01 mole, commercially available from Aldrich, Milwaukee, Wis.) and N-(3,4-dimethoxycinnamonitrile-alpha-phenyl)-N-phenylhydrazine (3.71 g, 0.01 mole) is refluxed in tetrahydrofuran (20 ml) for 16 hours with stirring. Upon removal of the solvent, the crude Compound (26) is isolated and purified by recrystallization.

Compound (27)

Compound (27) can be prepared by the procedure for Compound (26) except 0.02 mole of alpha-(4-chlorophenyl)-3,4-dimethoxycinnamonitrile is replaced with 0.02 mole of 4-chloro-alpha-(p-tolyl)-cinnamonitrile (CAS # 84434-79-7, commercially available from Aldrich, Milwaukee, Wis.).

E. Synthesis Relating to Carbazole N-phenylhydrazones

N-phenylhydrazine derivative

An N-phenylhydrazine derivative can be prepared according to the procedure similar to that described in Zh. Org. Khim. (1967), 3(9), 1605-3 by Matevosyan et el., which is incorporated herein by reference. To a mixture of phenylhydrazine (97 g, 0.9 mole, commercially available from Aldrich, Milwaukee, Wis.) and p-9-(4-chlorobenzylidene)fluorene (28.9 g, 0.1 mole, commercially available from Aldrich, Milwaukee, Wis.) heated to boiling temperature, sodium was slowly added until there was no more discharge of red coloration. After boiling for some time, the mixture was dissolved in 1750 ml of ethanol and cooled to −15° C. The precipitated product was recrystallized to give a hydrazine having the formula $H_2N$-$NR_1R_2$, wherein $R_1$ is phenyl and wherein $R_2$ is the group A, wherein A is represented by the formula

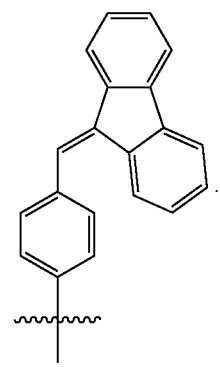

Compound (28)

9-Ethyl-3-carbolecarboxaldehyde (2.23 g, 0.01 mole, commercially available from Aldrich, Milwaukee, Wis.) and a hydrazine having the formula $H_2N$-$NR_1R_2$, wherein $R_1$ is phenyl and wherein $R_2$ is the group A wherein A is represented by the formula

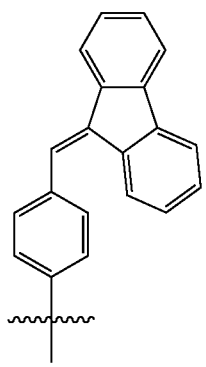

(3.6 g, 0.01 mole) is refluxed in tetrahydrofuran (20 ml) for 16 hours with stirring. Upon removal of the solvent, the crude Compound (28) is isolated and purified by recrystallization.

Compound (29)

Compound (29) can be prepared according to the following procedure. Carbozole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipithated is filtered off and the tetrahydrfuran layer is dried (MgSO$_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazolecarboxaldehyde.

9-Pentyl-3-carbazolecarboxaldehyde (2.65 g, 0.01 mol, commercially available from Aldrich, Milwaukee, Wis.) and a hydrazine having the formula H$_2$N-NR$_1$R$_2$, wherein R$_1$ is phenyl and wherein R$_2$ is the group A wherein A is represented by the formula

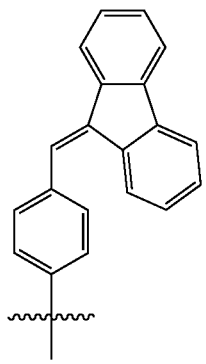

(3.6 g, 0.01 mole) is refluxed in tetrahydrofuran (20 ml) for 16 hours with stirring. Upon removal of the solvent, the crude Compound (29) is isolated and purified by recrystallization.

Compound (30)

Compound (30) can be prepared by the procedure for Compound (29) except 0.1 mole of 1-bromopentane is replaced with 0.1 mole of 1-bromodecane (commercially available from Aldrich, Milwaukee, Wis.).

Compound (31)

Compound (31) can be prepared by the procedure for Compound (28) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

F. Synthesis Relating to Carbazolecarboxaldehyde N-benzotriazolyl-N-phenylhydrazones N-(5-Benzotriazolyl)-N-phenylhydrazine N-(5-benzotriazolyl)-N-phenylhydrazine can be prepared according to the procedure described below. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time the mixture is cooled to room temperature. The product is isolated and purified.

Compound (32)

9-Ethyl-3-carbazolecarboxaldehyde (2.23 g, 0.01 mole, commercially available from Aldrich, Milwaukee, Wis.) and N-(5-benzotriazolyl)-N-phenylhydrazine (2.25 g, 0.01 mole) is refluxed in tetrahydrofuran (20 ml) for 16 hours with stirring. Upon removal of the solvent, the crude Compound (32) is isolated and purified by recrystallization.

Compound (33)

Compound (33) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipithated is filtered off and the tetrahydrofuran layer is dried (MgSO$_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazolecarboxaldehyde.

9-Pentyl-3-carbazolecarboxaldehyde (2.65 g, 0.01 mole, commercially available from Aldrich, Milwaukee, Wis.) and N-(5-benzotriazolyl)-N-phenylhydrazine (2.25 g, 0.01 mole) is refluxed in tetrahydrofuran (20 ml) for 16 hours with stirring. Upon removal of the solvent, the crude Compound (33) is isolated and purified by recrystallization.

Compound (34)

Compound (34) can be prepared by the procedure for Compound (33) except 0.1 mole of 1-bromopentane is replaced with 0.1 mole of 1-bromodecane (commercially available from Aldrich, Milwaukee, Wis.).

Compound (35)

Compound (35) can be prepared by the procedure for Compound (32) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

G. Synthesis Relating to Carbazolecarboxaldehyde Tetrazolylhydrazones

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599-608 by Atherton et el., which is incorporated herein by reference.

Compound (36)

9-Ethyl-3-carbazolecarboxaldehyde (2.23 g, 0.01 mole, commercially available from Aldrich, Milwaukee, Wis.) and 1-phenyl-1-(1-benzyl-1H-tetrazol-5-yl)hydrazine (2.66 g, 0.01 mole) is refluxed in tetrahydrofuran (20 ml) for 16 hours with stirring. Upon removal of the solvent, the crude Compound (36) is isolated and purified by recrystallization.

Compound (37)

Compound (37) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried ($MgSO_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazole-carboxaldehyde.

9-Pentyl-3-carbazolecarboxaldehyde (2.65 g, 0.01 mole, commercially available from Aldrich, Milwaukee, Wis.) and 1-phenyl-1-(1-benzyl-1H-tetrazol-5-yl)hydrazine (2.66 g, 0.01 mole) is refluxed in tetrahydrofuran (20 ml) for 16 hours with stirring. Upon removal of the solvent, the crude Compound (37) is isolated and purified by recrystallization.

Compound (38)

Compound (38) can be prepared by the procedure for Compound (37) except 0.1 mole of 1-bromopentane is replaced with 0.1 mole of 1-bromodecane (commercially available from Aldrich, Milwaukee, Wis.).

Compound (39)

Compound (39) can be prepared by the procedure for Compound (37) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

H. Synthesis Relating to Carbazolecarboxaldehyde Pyrazolylhydrazones

5-Methyl-1-Phenyl-3-(1-Phenylhydrazino)-Pyrazole 5-Methyl-1-phenyl-3-(1-phenylhydrazino)-pyrazole can be prepared according to the procedure described in J. Chem. Soc. C (1971), (12), 2314-17 by Boyd et el., which is incorporated herein by reference.

Compound (40)

9-Ethyl-3-carbazolecarboxaldehyde (2.23 g, 0.01 mole, commercially available from Aldrich, Milwaukee, Wis.) and 5-methyl-1-phenyl-3-(1-phenylhydrazino)-pyrazole (2.64 g, 0.01 mole) is refluxed in tetrahydrofuran (20 ml) for 16 hours with stirring. Upon removal of the solvent, the crude Compound (40) is isolated and purified by recrystallization.

Compound (41)

Compound (41) can be prepared according to the following procedure. Carbazole (16.7 g, 0.1 mol, commercially available from Aldrich, Milwaukee, Wis.), 1-bromopentane (15.1 g, 0.1 mol, commercially available from Aldrich, Milwaukee, Wis.), and benzyltriethyl ammonium chloride (1.7 g) are dissolved in tetrahydrofuran (60 mL) and a concentrated solution of sodium hydroxide (17 g) in water (17 mL) is added. The mixture is heated at reflux with strong mechanical stirring for 4 hours, then cooled to room temperature and poured into an excess of water. The solid that precipitated is filtered off and the tetrahydrofuran layer is dried ($MgSO_4$) and concentrated to dryness. The combined organic solids were recrystallized to form 9-pentylcarbazole.

Dimethylformamide (100 mL) is stirred and cooled in an ice bath while phosphorus oxychloride (35 mL, 58 g, 0.38 mol) is gradually added. 9-Pentylcarbazole (52 g, 0.22 mol) is introduced and the resulting mixture is heated on a steam bath with stirring for 1.5 hours. The entire mixture is cooled and added to water (200 mL) and the crude product is filtered off at the pump, washed with water (200 mL). The crude product is recrystallized to form 9-pentyl-3-carbazole-carboxaldehyde.

9-Pentyl-3-carbazolecarboxaldehyde (2.65 g, 0.01 mole, commercially available from Aldrich, Milwaukee, Wis.) and 5-methyl-1-phenyl-3-(1-phenylhydrazino)-pyrazole (2.64 g, 0.01 mole) is refluxed in tetrahydrofuran (20 ml) for 16 hours with stirring. Upon removal of the solvent, the crude Compound (41) is isolated and purified by recrystallization.

Compound (42)

Compound (42) can be prepared by the procedure for Compound (42) except 0.1 mole of 1-bromopentane is replaced with 0.1 mole of 1-bromodecane (commercially available from Aldrich, Milwaukee, Wis.).

Compound (43)

Compound (43) can be prepared by the procedure for Compound (41) except 0.01 mole of 9-Ethyl-3-carbazole-carboxaldehyde is replaced with 0.01 mole of 1-[9-(3-methylbutyl)-9H-carbazol-3-yl]-ethanone (commercially available from Interbioscreen Ltd., 121019 Moscow, P.O. Box 218, Moscow, Russia; web: www.ibscreen.com).

Compound (44)

Compound (44) can be prepared by the procedure for Compound (40) except 5-methyl-1-phenyl-3-(1-phenylhydrazino)-pyrazole (2.64 g, 0.01 mole) is replaced with 0.1 mole of 1-phenylhydrazino-pyrazole.

Compound (45)

Compound (45) can be prepared by the procedure for Compound (41) except 5-methyl-1-phenyl-3-(1-phenylhydrazino)-pyrazole (2.64 g, 0.01 mole) is replaced with 0.1 mole of 1-phenylhydrazino-pyrazole.

I. Synthesis Relating to Carbazolecarboxaldehyde Sulfonylphenylhydrazones

Compound (46)

9-Ethyl-3-carbazolecarboxaldehyde (2.23 g, 0.01 mole, commercially available from Aldrich, Milwaukee, Wis.) and 4-methylsulfonylphenylhydrazine (1.86 g, 0.01 mole, commercially available from Fisher Scientific USA, Pittsburgh, Pa.) is refluxed in tetrahydrofuran (20 ml) for 16 hours with stirring. Upon removal of the solvent, the crude Compound (46) is isolated and purified by recrystallization.

Compound (47)

9-Ethyl-3-carbazolecarboxaldehyde (2.23 g, 0.01 mole, commercially available from Aldrich, Milwaukee, Wis.) and 4-(methylsulfonyl)-2-nitrophenylhydrazine (2.31 g, 0.01 mole, commercially available from Aldrich, Milwaukee, Wis.) is refluxed in tetrahydrofuran (20 ml) for 16 hours with stirring. Upon removal of the solvent, the crude Compound (47) is isolated and purified by recrystallization.

Compound (48)

To a 500 ml 3-neck RPF equipped with mechanical stirrer and reflux condenser were added 7.69 g of 9-Pentyl-3-Carbazolecarboxaldehyde (0.03 mole, prepared in experimental section (B)) and 100 ml of tetrahydrofuran (THF). To a separate beaker were added 7.3 g of 4-Methylsulfonylphenylhydrazine hydrochloride (0.033 mole, obtained from Fisher Scientific USA, Pittsburgh, Pa.), 70 ml of THF, and then a solution of 5.52 g of K2CO3 in 25 ml of THF were added. This solution was added to the aldehyde solution and refluxed for 4 hours in the presence of few drops of concentrated sulfuric acid. TLC showed the disappearance of the starting materials and the appearance of the product. After the solution was cooled to RT, it was evaporated till dryness to obtain a yellow solid which was recrystalyzed 3 times from THF with activated charcoal used in all recrystalizations, and silica gel was added only to the third recrystalization. Obtained was 14 g (56% yield). H-NMR spectrum in CDCl3 was in agreement with the structure.

Compound (49)

Compound (49) can be prepared by the procedure for Compound (46) except 0.1 mole of 1-bromopentane is replaced with 0.1 mole of 1-bromodecane (commercially available from Aldrich, Milwaukee, Wis.).

Compound (50)

To a 100 ml RBF equipped with reflux condenser and magnetic stirrer were added, 16.6 g of 9-Pentyl-3-Carbazolecarboxaldehyde (0.061 mole, prepared as in experimental section B) and 50 ml of Ethanol were heated until all solid went into solution. 5 g of 1-aminopyrrole (prepared in experimental section A) was added and the solution was refluxed for five hours in the presence of few drops of glacial acetic acid. The solution was cooled to RT, then evaporated to dryness to obtain 10 g of the product (50% yield) H-NMR spectrum in CDCl3 was in agreement with the structure.

IV. Ionization Potential Protocol

Samples for ionization potential (Ip) measurements were prepared by dissolving Compounds 11, 12, 48, 50 independently in tetrahydrofuran. Each solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 µm. No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama, which is hereby incorporated by reference. The samples were illuminated with monochromatic light from the quartz monochromator with a deuterium lamp source. The power of the incident light beam was $2$-$5 \cdot 10^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open impute regime, for the photocurrent measurement. A $10^{-15}$-$10^{-12}$ amp photocurrent was flowing in the circuit under illumination. The photocurrent, I, was strongly dependent on the incident light photon energy hv. The $I^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama; and "Photoemission in Solids", Topics in Applied Physics, 26, 1-103. (1978) by M. Cordona and L. Ley]. The linear part of this dependence was extrapolated to the hv axis and Ip value was determined as the photon energy at the interception point. The ionization potential measurement has an error of ±0.03 eV. The ionization potential data are listed in Table 1.

V. Hole Mobility

Samples for charge carrier mobility measurements were prepared by dissolving Compounds 11, 12, 48, 50 independently in tetrahydrofuran with a binder to form 10% solid solutions. The binder was polycarbonate Z 200 (commercially obtained from Mitsubishi Engineering Plastics, White Plains N.Y.). The sample/binder ratio was 4:6 or 5:5. Each solution was coated on an aluminized polyester substrate to form a charge transport material (CTM) layer. The thickness of the CTM layer varied in the range of 5-10 µm.

The hole drift mobility was measured by a time of flight technique as described in "The discharge kinetics of negatively charged Se electrophotographic layers," Lithuanian Journal of Physics, 6, p. 569-576 (1966) by E. Montrimas, V. Gaidelis, and A. Pažera, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination was up to 1-5% of initial potential before illumination. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu = d^2/U_0 \cdot t_t$, where d is the layer thickness and $U_0$ is the surface potential at the moment of illumination.

Mobility values at electric field strength, E, of $6.4 \cdot 10^5$ V/cm are given in the Table 1. The mobility field dependencies may be approximated by the function $$\mu \sim e^{\alpha \sqrt{E}}$$

where $\alpha$ is parameter characterizing mobility field dependence. The value of the parameter $\alpha$ is also given in Table 1.

TABLE 1

| Compound | Mobility (cm²/Vs) | α | $I_p$ (eV) |
|---|---|---|---|
| 12 | $1.6 \times 10^{-8}$ | 0.0063 | 5.55 |
| 48 | $1.7 \times 10^{-8}$ | 0.0065 | — |
| 50 | No signal | — | 5.74 |
| 11 | $1.2 \times 10^{-8}$ | — | 5.62 |

It is well understood in the art that variations in substitution, variations in additives, variations in processes and apparatus of use, and conditions and proportions may be varied to achieve variations in performance within the control of the ordinarily skilled artisan. The examples and the disclosure represent a generic disclosure intended to include those variations, and the claims represent a descriptions of the invention including those variations. Those variations and all generic embodiments of the invention are intended to be included within the following claims.

What is claimed is:

1. An organophotoreceptor comprising:

a) a charge transport compound having the formula

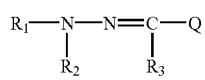

where $R_1$ comprises an aryl group and $R_2$ comprises a group selected from the group consisting of sulfolanyl, pyrrolyl, pyrazolyl, benzotriazolyl, stilbenyl, tetrazolyl group, and group A, wherein A is represented by the structure

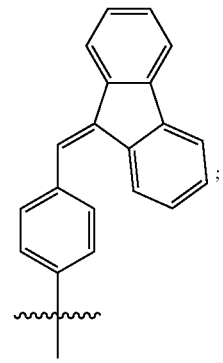

or $R_1$ is a hydrogen atom or an alkyl moiety, and $R_2$ comprises a sulfonylphenyl group bonded through a phenyl carbon to the nitrogen, wherein the nitrogen is bonded at the 4-position on the phenyl ring;

$R_3$ is hydrogen, an alkyl group, an aryl group, or a hydrocarbon group; and

Q is a 3-carbazole group;

(b) a charge generating compound; and (c) an electrically conductive substrate.

2. The organophotoreceptor of claim 1 wherein $R_2$ comprises a sulfolanyl group.

3. The organophotoreceptor of claim 2 wherein the charge transport compound has a central nucleus of the formula:

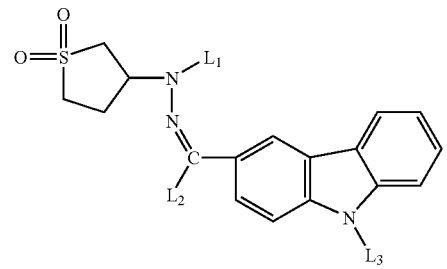

wherein $L_1$ comprises an aryl group, and $L_2$ and $L_3$ are independently selected from the group consisting of hydrogen and hydrocarbons.

4. The organophotoreceptor of claim 1 wherein $R_2$ comprises group A, wherein A is represented by the structure

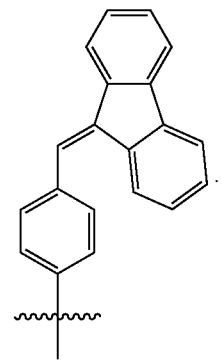

5. The organophotoreceptor of claim 4 wherein the charge transport compound has a central nucleus of the formula;

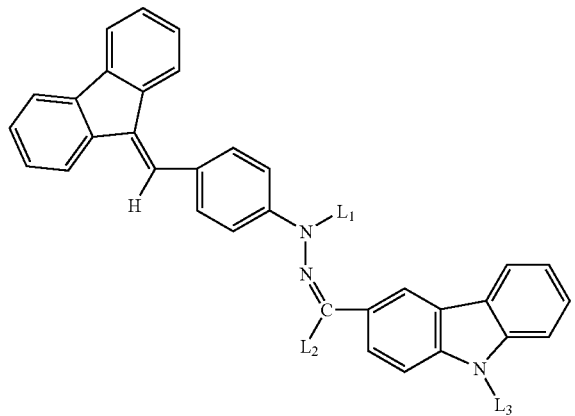

wherein $L_1$ comprises an aryl group, and $L_2$ and $L_3$ are independently selected from the group consisting of hydrogen and hydrocarbons.

6. The organophotoreceptor of claim 1 wherein $R_2$ comprises a pyrrolyl group.

7. The organophotoreceptor of claim 6 wherein the charge transport compound has a central nucleus of the formula:

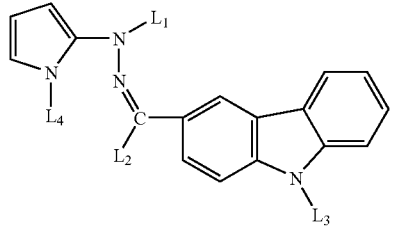

wherein $L_1$ comprises an aryl group, and $L_2$ and $L_3$ are independently selected from the group consisting of hydrogen and hydrocarbons, and $L_4$ is hydrogen.

8. The organophotoreceptor of claim 1 wherein $R_2$ comprises a pyrazolyl group.

9. The organophotoreceptor of claim 8 wherein the charge transport compound has a central nucleus of the formula:

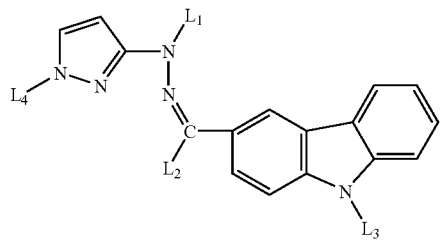

wherein $L_1$ comprises an aryl group, and $L_2$ and $L_3$ are independently selected from the group consisting of hydrogen and hydrocarbons, and $L_4$ is independently selected from the group consisting of hydrogen and phenyl.

10. The organophotoreceptor of claim 1 wherein $R_2$ comprises a benzotriazolyl group.

11. The organophotoreceptor of claim 10 wherein the charge transport compound has a central nucleus of the formula:

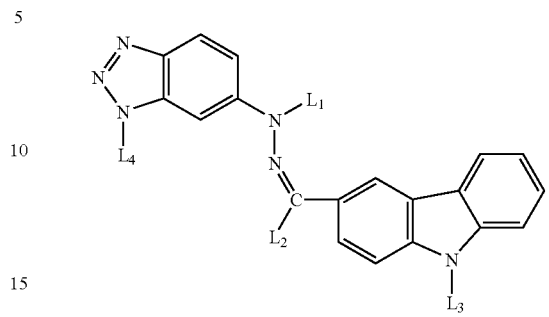

wherein $L_1$ comprises an aryl group, and $L_2$ and $L_3$ are independently selected from the group consisting of hydrogen and hydrocarbons, and $L_4$ is hydrogen.

12. The organophotoreceptor of claim 1 wherein $R_2$ comprises a stilbenyl group.

13. The organophotoreceptor of claim 12 wherein the charge transport compound has a central nucleus of the formula:

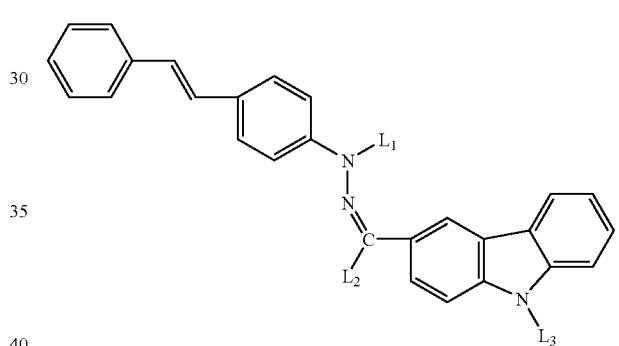

wherein $L_1$ comprises an aryl group, and $L_2$ and $L_3$ are independently selected from the group consisting of hydrogen and hydrocarbons.

14. The organophotoreceptor of claim 1 wherein $R_2$ comprises a tetrazolyl group.

15. The organophotoreceptor of claim 14 wherein the charge transport compound has a central nucleus of the formula:

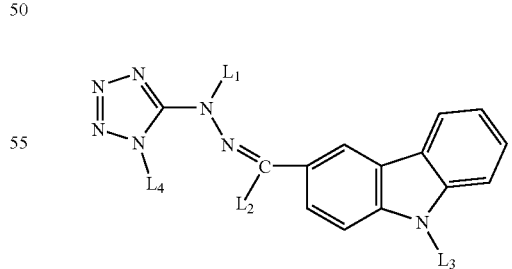

wherein $L_1$ comprises an aryl group, and $L_2$ and $L_3$ are independently selected from the group consisting of hydrogen and hydrocarbons, and $L_4$ is independently selected from the group consisting of hydrogen and phenylmethylene wherein the phenylinethylene is bonded to the nitrogen atom through the methyl carbon.

16. The organophotoreceptor of claim 1 wherein R₁ is a hydrogen atom or an alkyl moiety, and R₂ comprises a sulfonylphenyl group bonded through a phenyl carbon to the nitrogen, wherein the nitrogen is bonded at the 4-position on the phenyl ring.

17. The organophotoreceptor of claim 16 wherein the charge transport compound has a central nucleus of the formula:

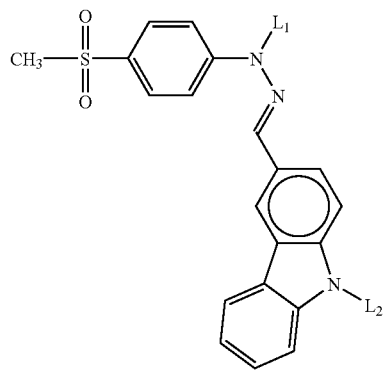

wherein L₁ a hydrogen atom or alkyl moiety, and L₂ is selected from the group consisting of hydrocarbons.

18. An organophotoreceptor according to claim 1 wherein said organophotoreceptor is in the form of a flexible belt.

19. An organophotoreceptor according to claim 1 comprising:
(a) a charge transport layer comprising said charge transport compound and a polymeric binder;
(b) a charge generating layer comprising said charge generating compound and a polymeric binder; and
(c) said electrically conductive substrate.

20. An organophotoreceptor according to claim 1 wherein said charge transport compound is a compound selected from the group consisting of,

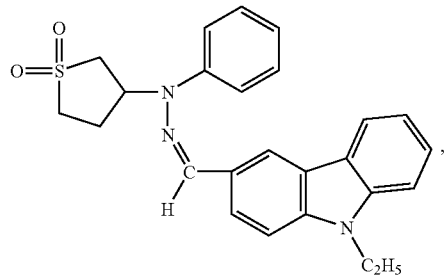

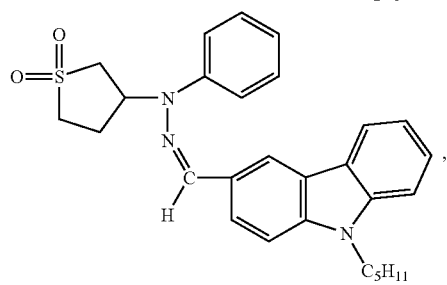

-continued

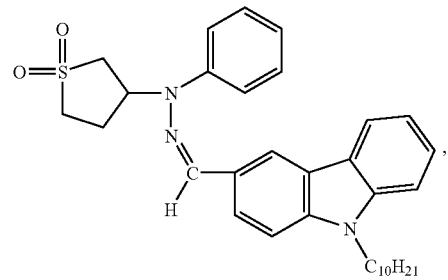

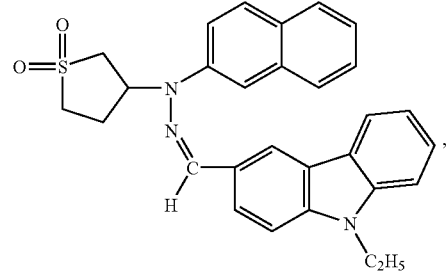

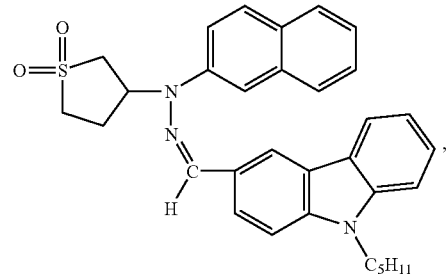

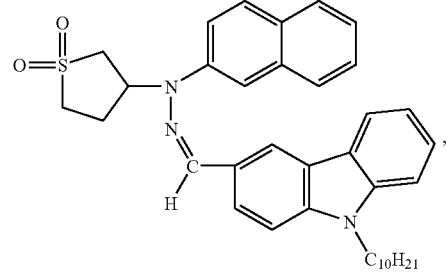

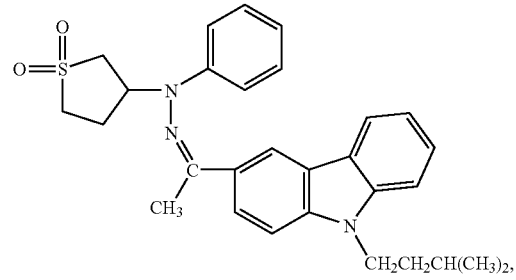

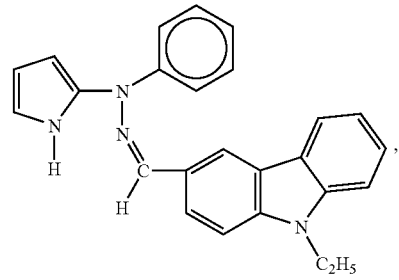

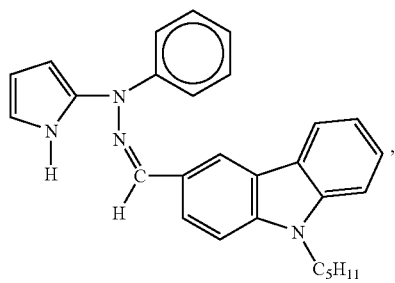
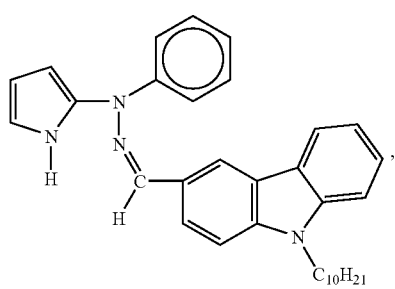
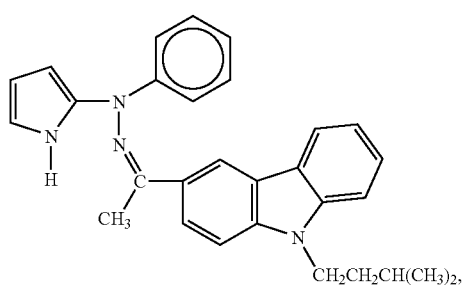
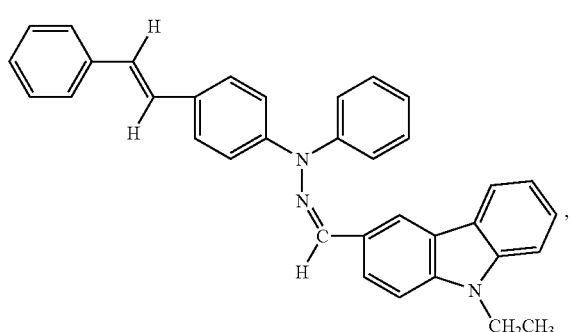
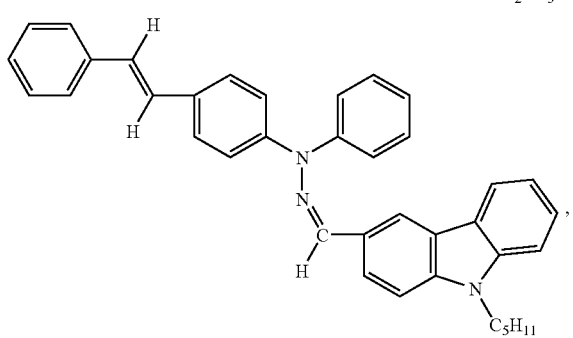
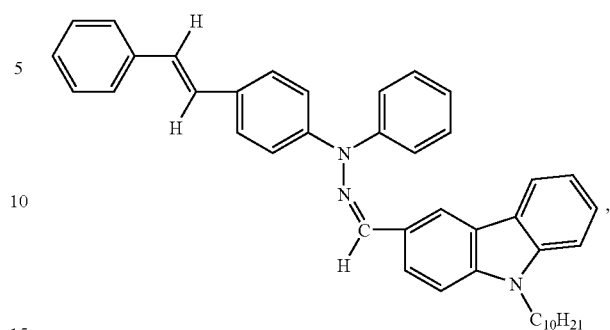
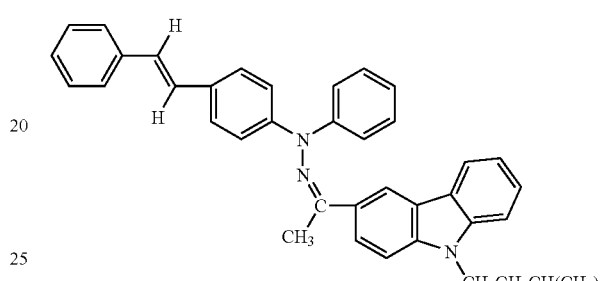
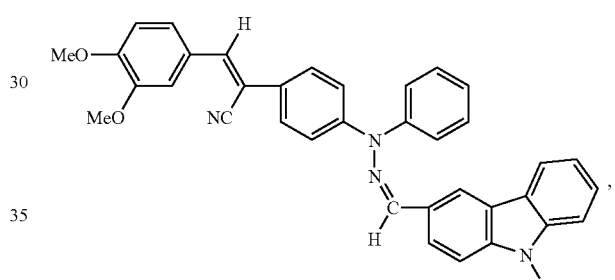
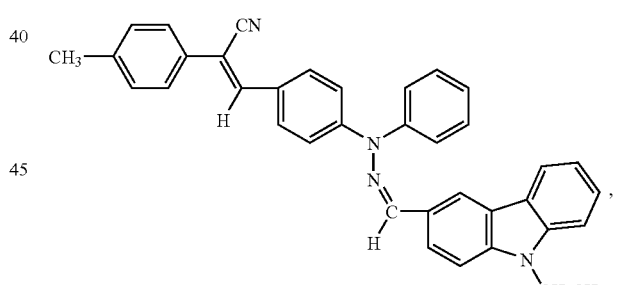
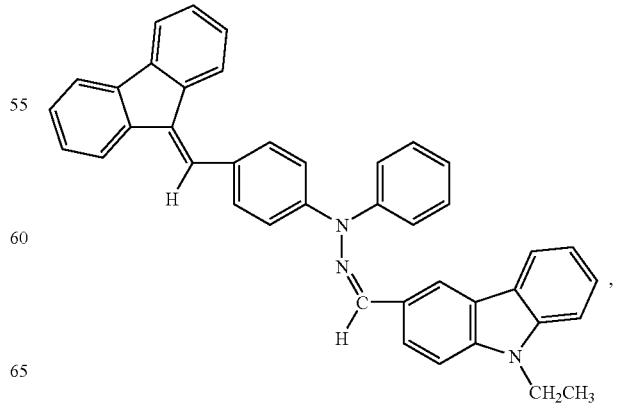

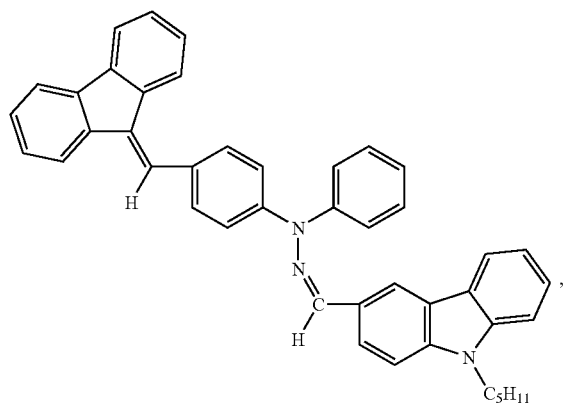
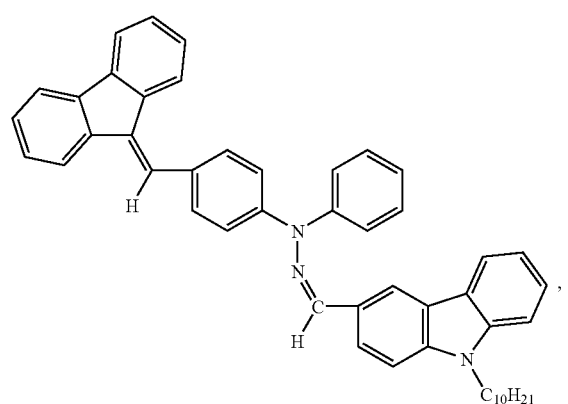
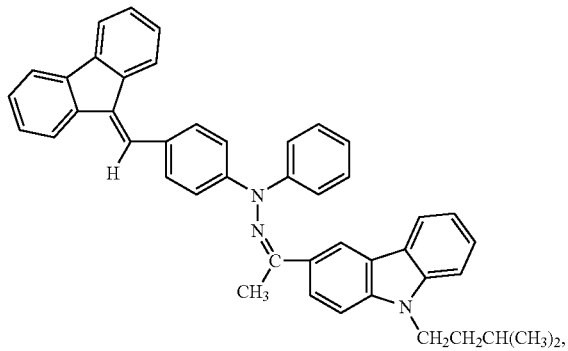
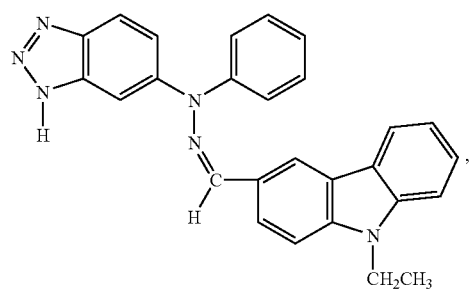
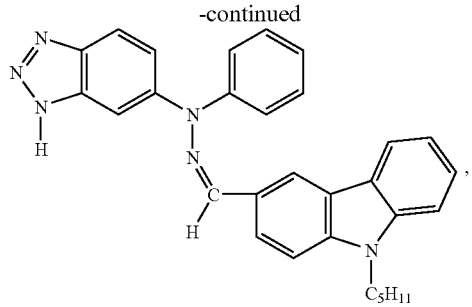
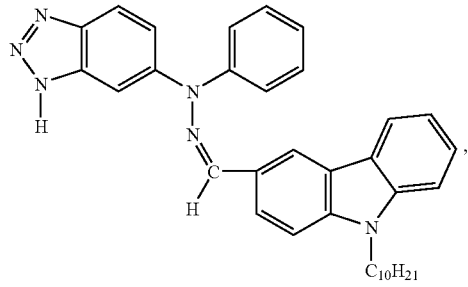
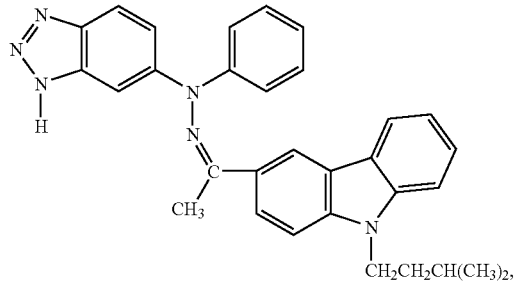
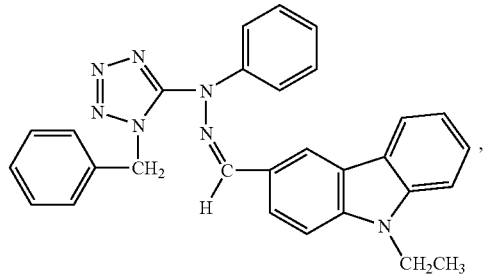
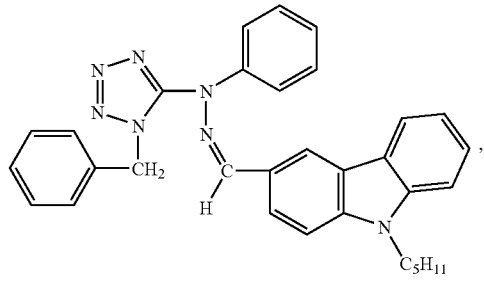
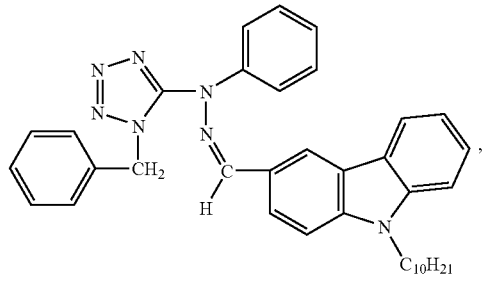

-continued
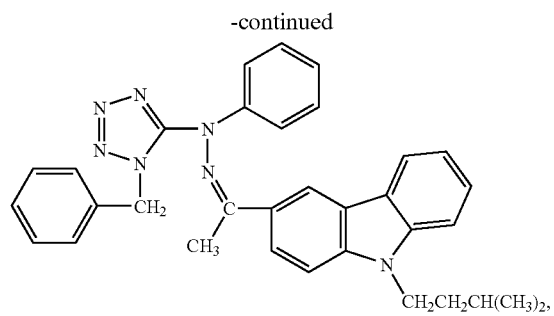
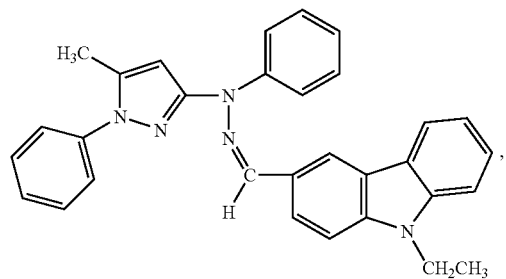
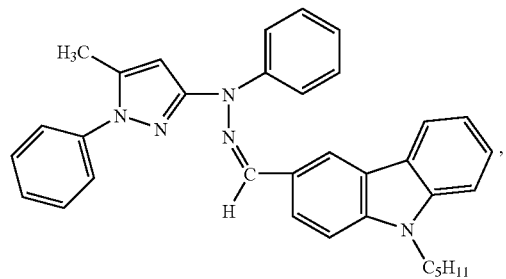
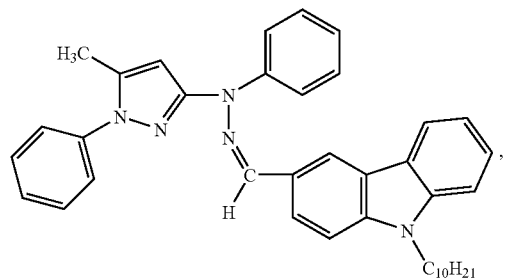
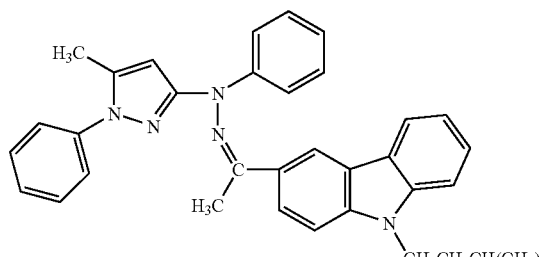
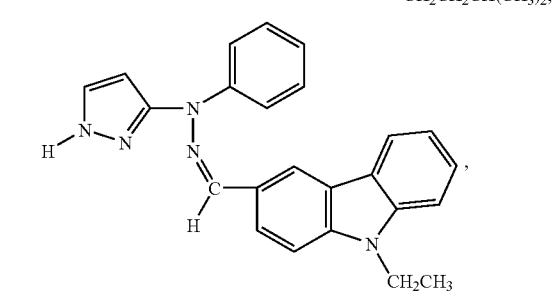
-continued
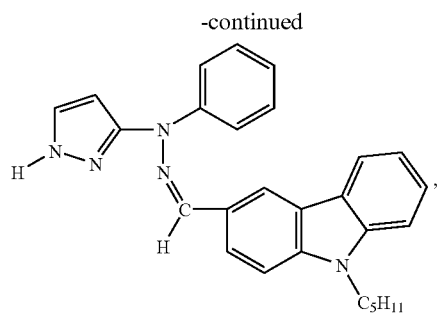
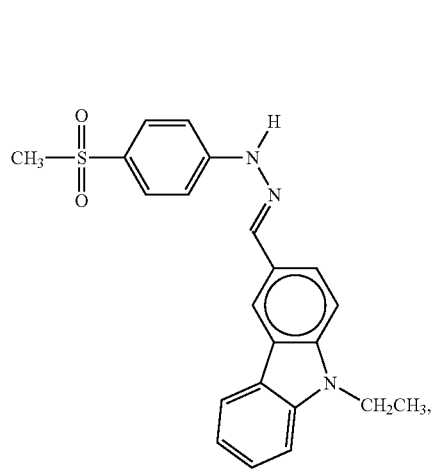
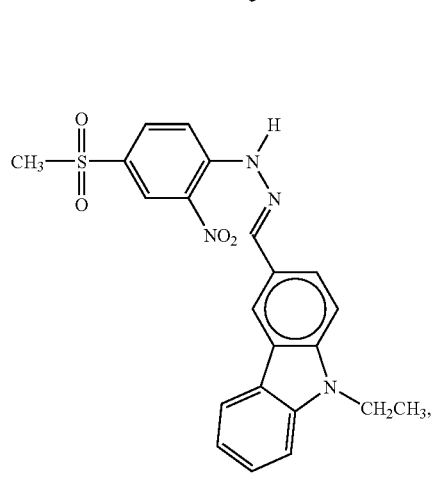
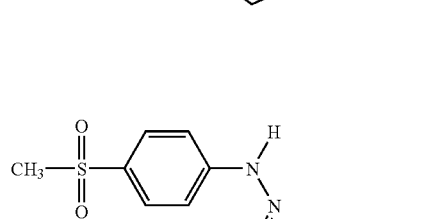
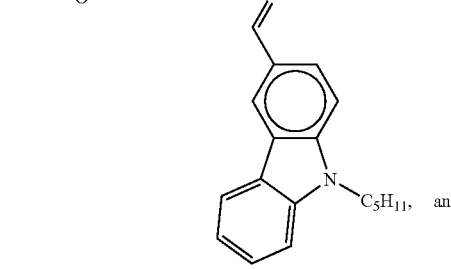, and -continued

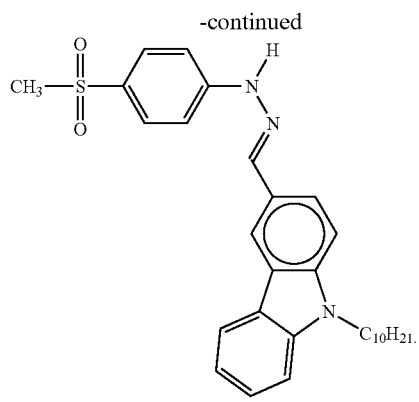

21. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 1.

22. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 3.

23. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 5.

24. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 7.

25. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 9.

26. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 11.

27. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 13.

28. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 15.

29. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 17.

30. An organophotoreceptor comprising:
a) a charge transport compound having the formula

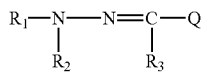

where $R_1$ comprises an aryl group and $R_2$ comprises a group selected from the group consisting of sulfolanyl, pyrrolyl, pyrazolyl, benzotriazolyl, stilbenyl, tetrazolyl group, and group A, wherein A is represented by the structure

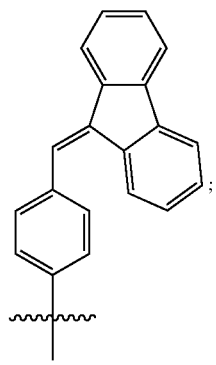

$R_3$ is hydrogen, an alkyl group, an aryl group, a heterocyclic group or a hydrocarbon group; and
Q is a 3-carbazole group;
(b) a charge generating compound; and
(c) an electrically conductive substrate.

31. An organophotoreceptor comprising:
a) a charge transport compound having the formula

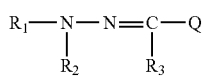

where $R_1$ comprises an aryl group and $R_2$ comprises a group selected from the group consisting of sulfolanyl, pyrrolyl, pyrazolyl, benzotriazolyl, stilbenyl, tetrazolyl group, and group A, wherein A is represented by the structure

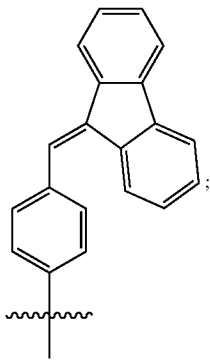

or R₁ comprises hydrogen atom, an alkyl group, or an aryl group and R₂ comprises a sulfonylphenyl group bonded through a phenyl carbon to the nitrogen, wherein the nitrogen is bonded at the 4-position on the phenyl ring;
R₃ is an alkyl group, an aryl group, or a hydrocarbon group; and
Q is a 3-carbazole group;
(b) a charge generating compound; and
(c) an electrically conductive substrate.

32. The organophotoreceptor of claim 31 wherein R₁ comprises an aryl group and R₂ comprises a sulfolanyl group.

33. An organophotoreceptor according to claim 31 wherein said organophotoreceptor is in the form of a flexible belt.

34. An organophotoreceptor according to claim 31 comprising:
(a) a charge transport layer comprising said charge transport compound and a polymeric binder;
(b) a charge generating layer comprising said charge generating compound and a polymeric binder; and
(c) said electrically conductive substrate.

35. An electrophotographic imaging apparatus comprising:
(a) a plurality of support rollers; and
(b) an organophotoreceptor in the form of a flexible belt threaded around said support rollers, said organophotoreceptor comprising the organophotoreceptor of claim 31.

36. An electrophotographic imaging apparatus comprising:
(a) a plurality of support rollers; and
(b) an organophotoreceptor in the form of a flexible belt threaded around said support rollers, said organophotoreceptor comprising the organophtoreceptor of claim 32.

* * * * *